(12) United States Patent
Horacek

(10) Patent No.: US 8,182,489 B2
(45) Date of Patent: May 22, 2012

(54) METHOD AND APPARATUS FOR PERFORMING AN OPEN WEDGE OSTEOTOMY

(75) Inventor: Justin L. Horacek, Boulder, CO (US)

(73) Assignee: Arthrex, Inc., Naples, FL (US)

( * ) Notice: Subject to any disclaimer, the term of this patent is extended or adjusted under 35 U.S.C. 154(b) by 958 days.

(21) Appl. No.: 12/188,058

(22) Filed: Aug. 7, 2008

(65) Prior Publication Data

US 2009/0043308 A1 Feb. 12, 2009

Related U.S. Application Data

(60) Provisional application No. 60/963,720, filed on Aug. 7, 2007.

(51) Int. Cl.
*A61F 5/00* (2006.01)
(52) U.S. Cl. .................. 606/87; 606/84; 623/17.11
(58) Field of Classification Search .............. 623/17.11, 623/17.16; 606/321, 84, 87
See application file for complete search history.

(56) References Cited

U.S. PATENT DOCUMENTS

| | | | | |
|---|---|---|---|---|
| 5,766,251 A | * | 6/1998 | Koshino | 623/11.11 |
| 5,865,847 A | * | 2/1999 | Kohrs et al. | 128/898 |
| 5,947,968 A | * | 9/1999 | Rogozinski | 623/17.16 |
| 2002/0038123 A1 | * | 3/2002 | Visotsky et al. | 606/73 |

* cited by examiner

*Primary Examiner* — Andrew Yang
(74) *Attorney, Agent, or Firm* — Dickstein Shapiro LLP

(57) ABSTRACT

A method for performing an open wedge osteotomy, the method comprising:
  forming a cut in a bone;
  manipulating the portions of the bone adjacent to the cut so as to open the cut into a wedge-like opening;
  providing an osteotomy implant, wherein the osteotomy implant comprises:
    an elongated body characterized by a distal end and proximal end, the elongated body having a screw thread thereon;
  positioning at least the distal end of the elongated body into the wedge-like opening so that the screw thread engages the surrounding bone; and
  threadingly advancing the elongated body into the wedge-like opening until the portions of the bone assume the desired positioning, with the elongated body stabilizing the bone portions in this position.

19 Claims, 42 Drawing Sheets

METHOD AND APPARATUS FOR PERFORMING AN OPEN WEDGE OSTEOTOMY

REFERENCE TO PENDING PRIOR PATENT APPLICATION

This patent application claims benefit of pending prior U.S. Provisional Patent Application Ser. No. 60/963,720, filed Aug. 7, 2007 by Justin L. Horacek for DESCRIPTION OF A BONE FUSION IMPLANT AND VARIATIONS THEREOF, which patent application is hereby incorporated herein by reference.

FIELD OF THE INVENTION

This invention relates to surgical methods and apparatus in general, and more particularly to surgical methods and apparatus for performing open wedge osteotomies of the knee.

BACKGROUND OF THE INVENTION

Osteotomies of the knee are an important technique for treating knee osteoarthritis. In essence, knee osteotomies adjust the geometry of the knee joint so as to transfer weight bearing load from arthritic portions of the joint to relatively unaffected portions of the joint.

Knee osteotomies are also an important technique for addressing abnormal knee geometries, e.g., due to birth defect, injury, etc.

Most knee osteotomies are designed to modify the geometry of the tibia, so as to adjust the manner in which load is transferred across the knee joint.

There are essentially two ways in which to adjust the orientation of the tibia: (i) the so-called "closed wedge" technique; and (ii) the so-called "open wedge" technique.

With the closed wedge technique, a wedge of bone is removed from the upper portion of the tibia, and then the tibia is manipulated so as to close the resulting gap, whereby to re-orient the lower portion of the tibia relative to the tibial plateau and hence adjust the manner in which load is transferred from the femur to the tibia.

With the open wedge technique, a cut is made into the upper portion of the tibia, the tibia is manipulated so as to open a wedge-like opening in the bone, and then the bone is secured in this position (e.g., by screwing metal plates to the bone or by inserting a wedge-shaped implant into the opening in the bone), whereby to re-orient the lower portion of the tibia relative to the tibial plateau and hence adjust the manner in which load is transferred from the femur to the tibia.

While both closed wedge osteotomies and open wedge osteotomies provide substantial benefits to the patient, they are procedurally challenging for the surgeon.

Among other things, with respect to open wedge osteotomies, it can be difficult to properly stabilize the upper and lower portions of the tibia relative to one another, and to properly maintain them in this position, while healing occurs.

In addition, with open wedge osteotomies, the wedge-shaped implants are generally anatomically-specific, in the sense that the size of the implant must be matched to the size of the anatomy and the degree of correction desired. This can present inventory issues.

And, with open wedge osteotomies, the wedge-shaped implants are generally procedure-specific, in the sense that an antero-medial approach may require one configuration for the implant, a lateral approach may require another configuration for the implant, etc. Again, this can present inventory issues.

In addition to the foregoing, open wedge osteotomies may also be performed on locations other than the high tibia. By way of example but not limitation, an open wedge knee osteotomy may be performed on the low femur. By way of further example but not limitation, an open wedge osteotomy may be performed on a joint other than the knee, e.g., an open wedge osteotomy may be performed on the elbow. Again, these open wedge osteotomies may be stabilized with metal plates, wedge-shaped implants, etc. And again, these open wedge osteotomies generally suffer from the aforementioned issues of proper stabilization, size specificity, procedure specificity, etc.

The present invention is directed to open wedge osteotomies in general, both for the knee and for other joints, and is intended to provide a new and improved osteotomy implant which addresses the foregoing issues with the prior art.

SUMMARY OF THE INVENTION

The present invention comprises a novel method and apparatus for performing an open wedge osteotomy. More particularly, the present invention comprises the provision and use of a novel method for performing an open wedge osteotomy, the method comprising:

forming a cut in a bone;

manipulating the portions of the bone adjacent to the cut so as to open the cut into a wedge-like opening;

providing an osteotomy implant, wherein the osteotomy implant comprises:

an elongated body characterized by a distal end and proximal end, the elongated body having a screw thread thereon;

positioning at least the distal end of the elongated body into the wedge-like opening so that the screw thread engages the surrounding bone; and threadingly advancing the elongated body into the wedge-like opening until the portions of the bone assume the desired positioning, with the elongated body stabilizing the bone portions in this position.

In another form of the present invention, there is provided a method for performing an open wedge osteotomy, the method comprising:

forming a cut in a bone;

manipulating the portions of the bone adjacent to the cut so as to open the cut into a wedge-like opening;

providing an osteotomy implant, wherein the osteotomy implant comprises:

an elongated body characterized by a distal end and proximal end, the elongated body having a bone anchoring mechanism associated therewith;

positioning at least the distal end of the elongated body into the wedge-like opening so that it engages the surrounding bone; and advancing the elongated body into the wedge-like opening until the portions of the bone assume the desired positioning, with the bone anchoring mechanism preventing retraction of the elongated body from the wedge-like opening and with the elongated body stabilizing the bone portions in this position.

In another form of the present invention, there is provided apparatus for performing an open wedge osteotomy, the apparatus comprising:

an osteotomy implant for disposition in a wedge-shaped opening created in the bone, the osteotomy implant comprising:

an elongated body characterized by a distal end and a proximal end, and having a screw thread for engaging the surrounding bone; and an osteotomy plate for covering at least a portion of the entrance of the wedge-like opening.

In another form of the present invention, there is provided apparatus for performing an open wedge osteotomy, the apparatus comprising:

an osteotomy implant for disposition in a wedge-shaped opening created in the bone, the osteotomy implant comprising:

an elongated body characterized by a distal end and a proximal end, and having a bone anchoring mechanism associated therewith for engaging the surrounding bone, with the bone anchoring mechanism preventing retraction of the elongated body from the wedge-like opening; and an osteotomy plate for covering at least a portion of the entrance of the wedge-like opening.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention provides a novel osteotomy implant for use in an open wedge osteotomy. More particularly, after a cut has been made in the bone, and after the bone is manipulated so as to open a wedge-like opening in the bone, the osteotomy implant is disposed in the wedge-like opening in the bone so as to stabilize the bone portions in a desired (i.e., corrected) position. Significantly, the novel osteotomy implant may be used in substantially any open wedge osteotomy, e.g., a knee osteotomy, an elbow osteotomy, etc., and the novel osteotomy implant may be used with substantially any bone, e.g., the high tibia, the low femur, etc. For clarity of illustration, the novel osteotomy implant may hereinafter be discussed in the context of an open wedge, high tibial osteotomy, however, it should be appreciated that this is solely for the sake of illustration and should not be construed as a limitation of the present invention.

Figure 1:
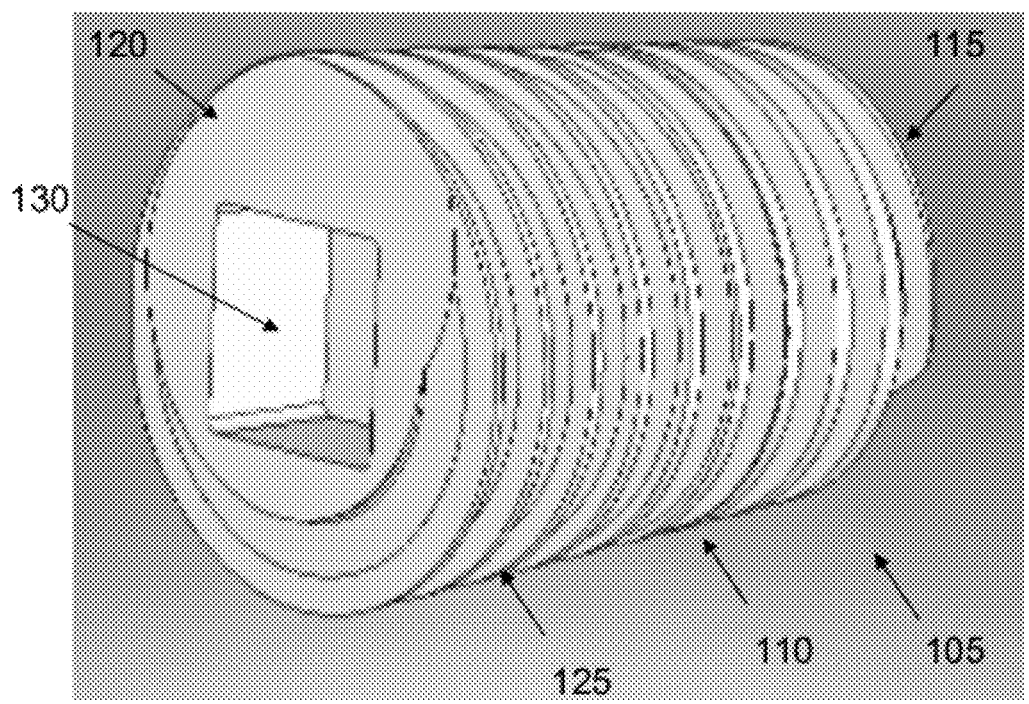
FIGS. 1 and 2 are schematic views showing a first novel osteotomy implant formed in accordance with the present invention.
Figure 2:
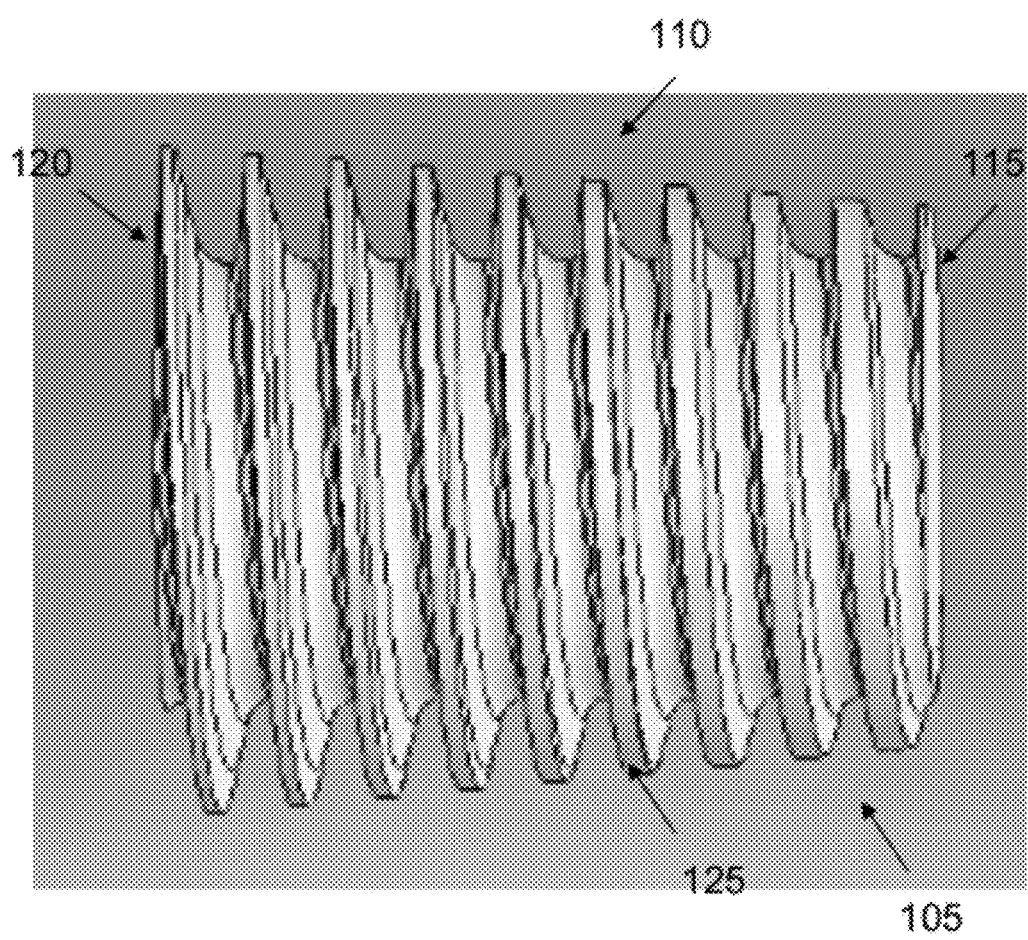

Looking now at FIGS. 1 and 2, there is shown a novel osteotomy implant 105 intended to be deployed in an open wedge osteotomy so as to stabilize the bone portions in a desired (i.e., corrected) position. Osteotomy implant 105 generally comprises an elongated body 110 having a distal end 115 and a proximal end 120. Elongated body 110 is preferably tapered, increasing in diameter as it extends distal to proximal. Elongated body 110 comprises a screw thread 125 for engaging bone. Proximal end 120 may be provided with a recess 130 for mating with a driver (not shown) for turning osteotomy implant 105 into bone, as will hereinafter be discussed. In this respect, it should be appreciated that recess 130 may have substantially any geometry appropriate for transferring rotation from the drive to the osteotomy implant 105, e.g., it may have the square configuration shown in FIG. 1, or it may have a hex geometry, an ovoid geometry, or substantially any other non-circular geometry, etc.

Figure 3:
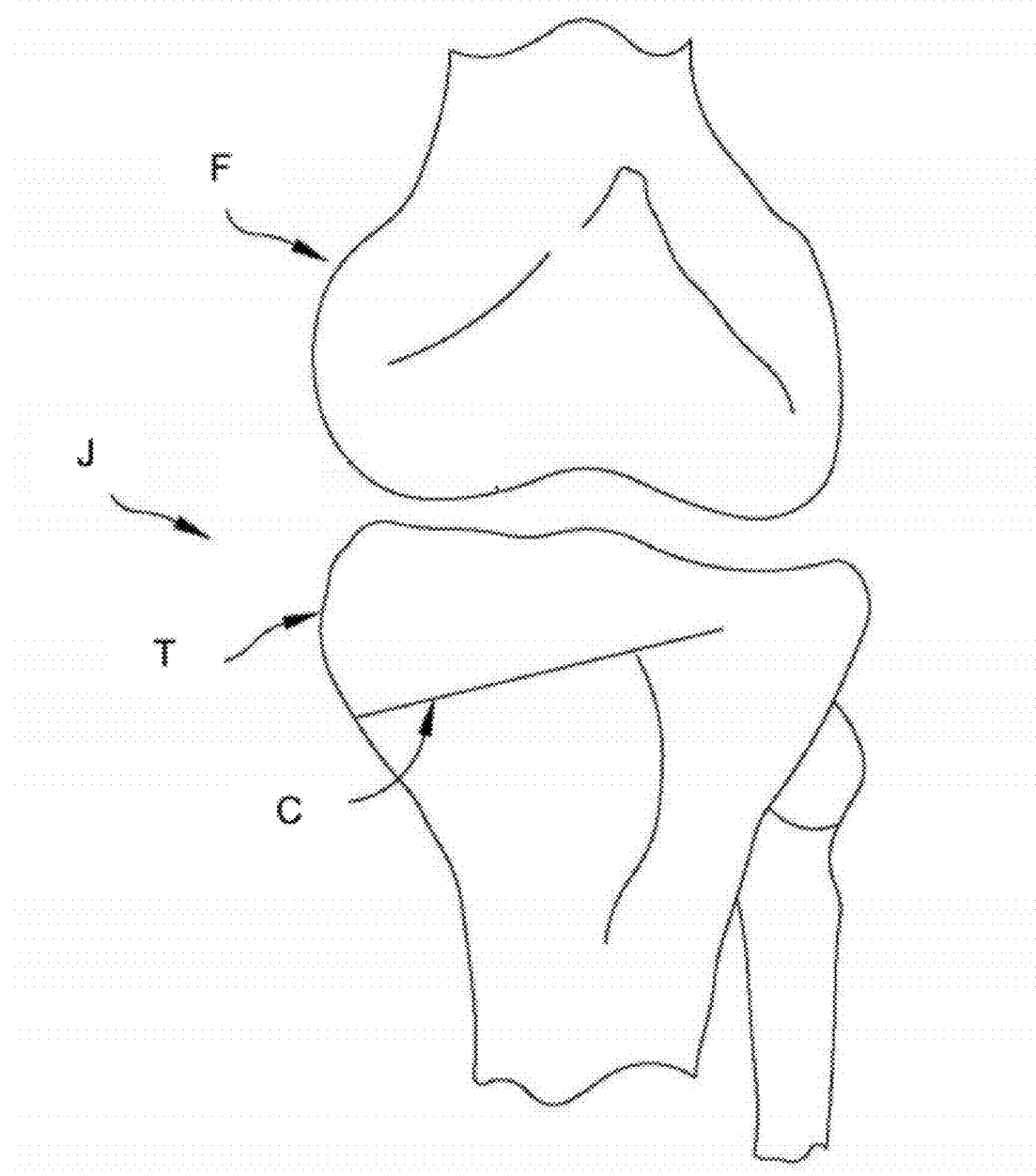
FIGS. 3 and 4 are schematic views showing a traditional osteotomy cut procedure to create a wedge-like opening in the bone.
Figure 4:
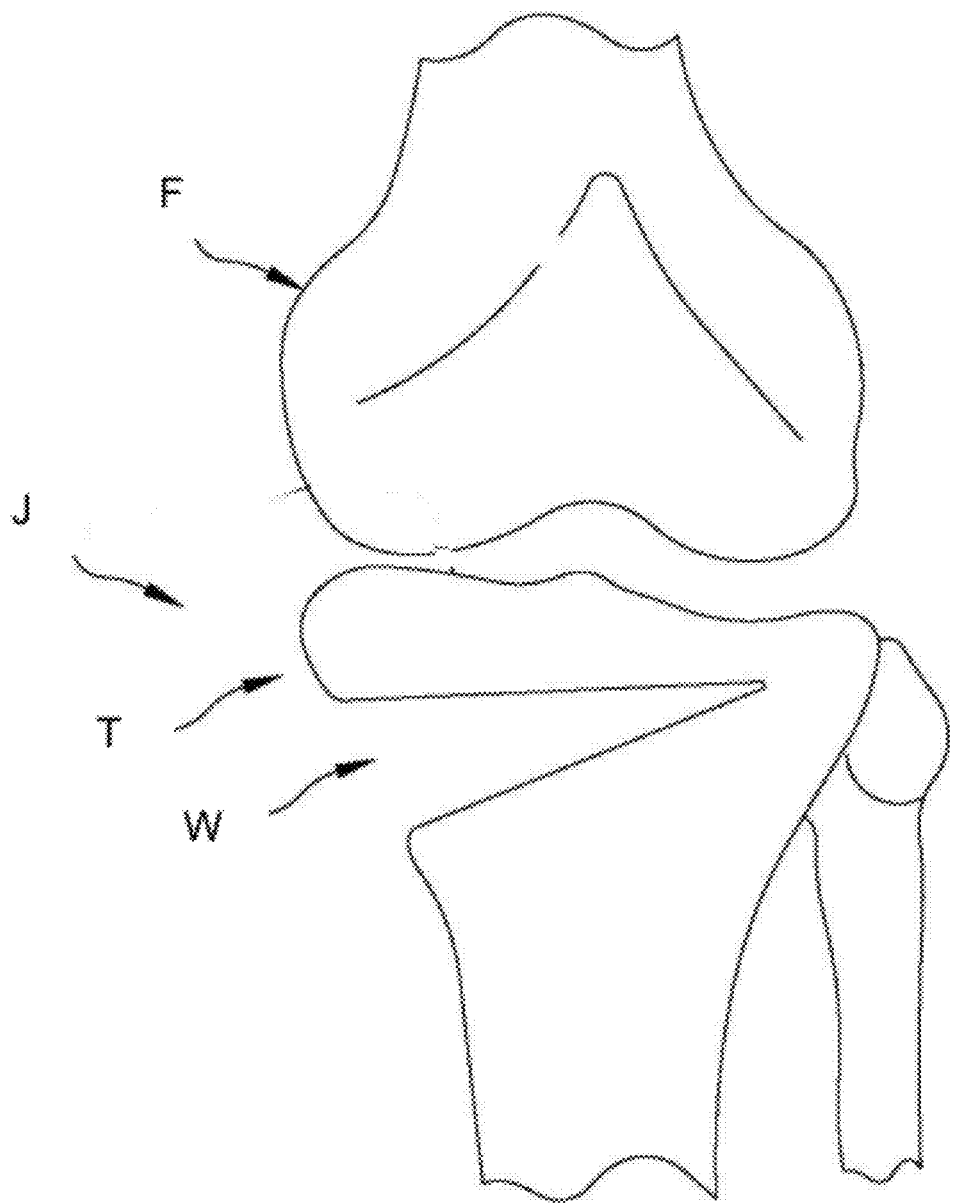

In use, osteotomy implant 105 is intended to be deployed in an open wedge osteotomy so as to secure the bone in a corrected position. More particularly, and looking now at FIG. 3, there is shown a knee joint J upon which an open wedge osteotomy is to be performed. Knee joint generally comprises a tibia T and a femur F. In accordance with the present invention, the open wedge osteotomy is effected by first making a cut C into the upper tibia, and then manipulating the lower portion of the tibia so as to open a wedge-like opening W (FIG. 4) in the bone, with the wedge-like opening W being configured so as to adjust the manner in which load is transferred from the femur to the tibia. In this respect, it should be appreciated that a variety of methods are well known in the art for determining the degree of correction necessary to correctly re-align the weight-bearing axis of the knee. Furthermore, cut C and wedge-like opening W may be formed in a variety of ways well known in the art.

Figure 5:
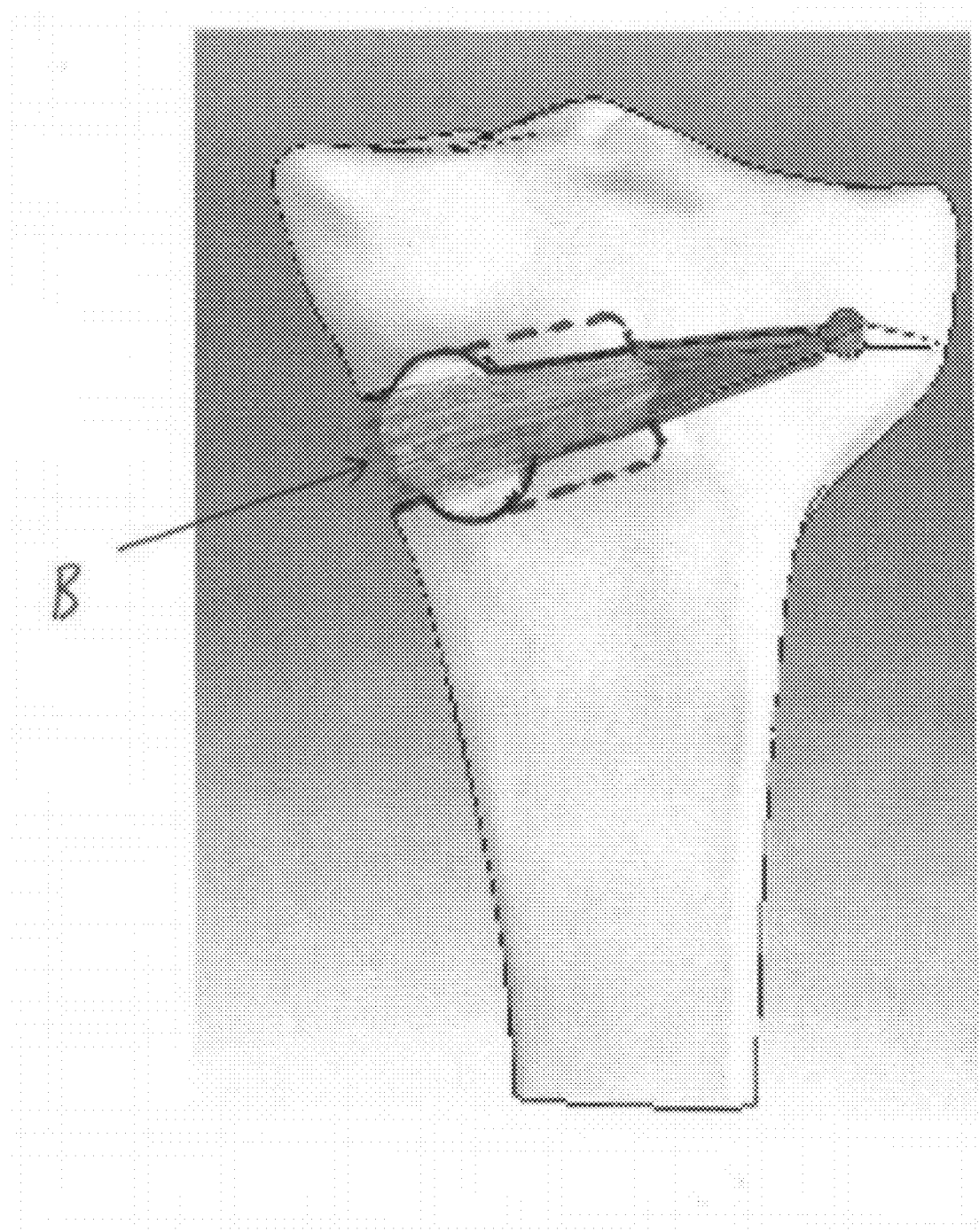
FIG. 5 is a schematic view showing a bore formed along the wedge-like opening.

In order to prepare the tibia to receive the osteotomy implant, a bore B is preferably formed in the tibia by over-drilling wedge-like opening W (FIG. 5). Bore B is preferably sized so to be just slightly larger than the diameter of the distal end of the osteotomy implant, and just slightly smaller than the diameter of the proximal end of the osteotomy implant, in order that the implant may be easily inserted into bore B and make a gripping engagement with tibia T.

Figure 6:
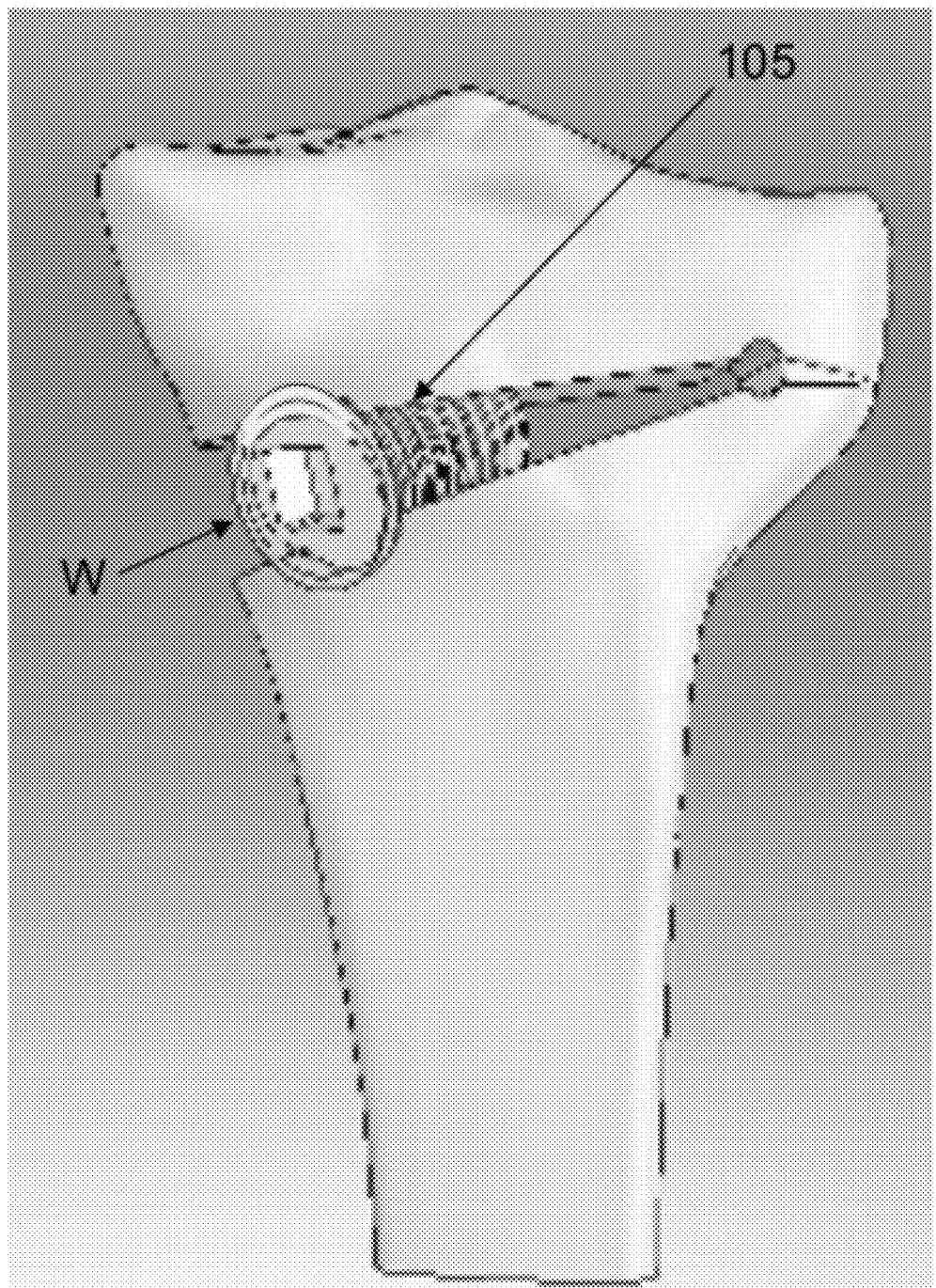
FIGS. 6 and 7 are schematic views showing the osteotomy implant of FIGS. 1 and 2 positioned within an osteotomy cut formed in the tibia.
Figure 7:
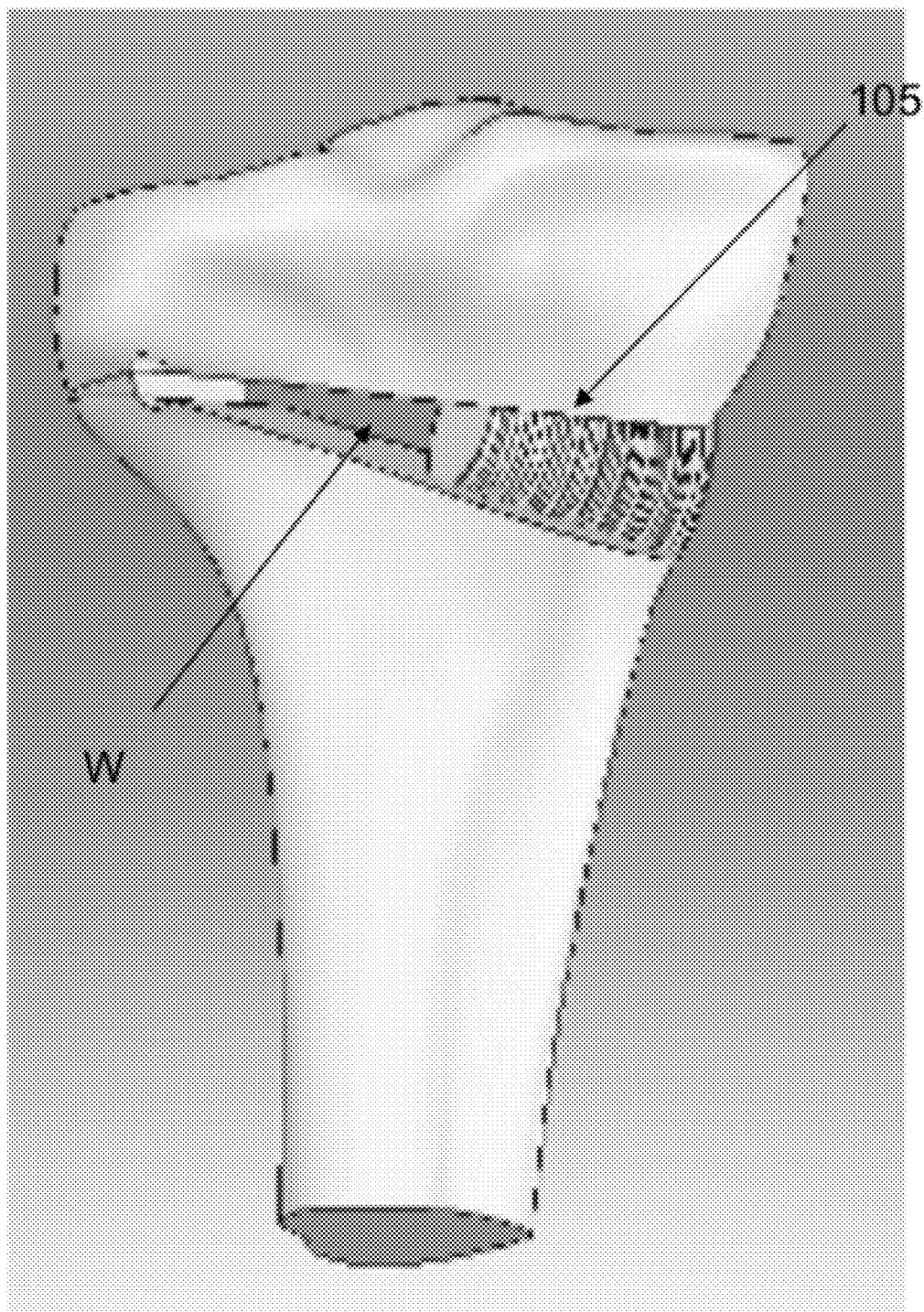
Figure 8:
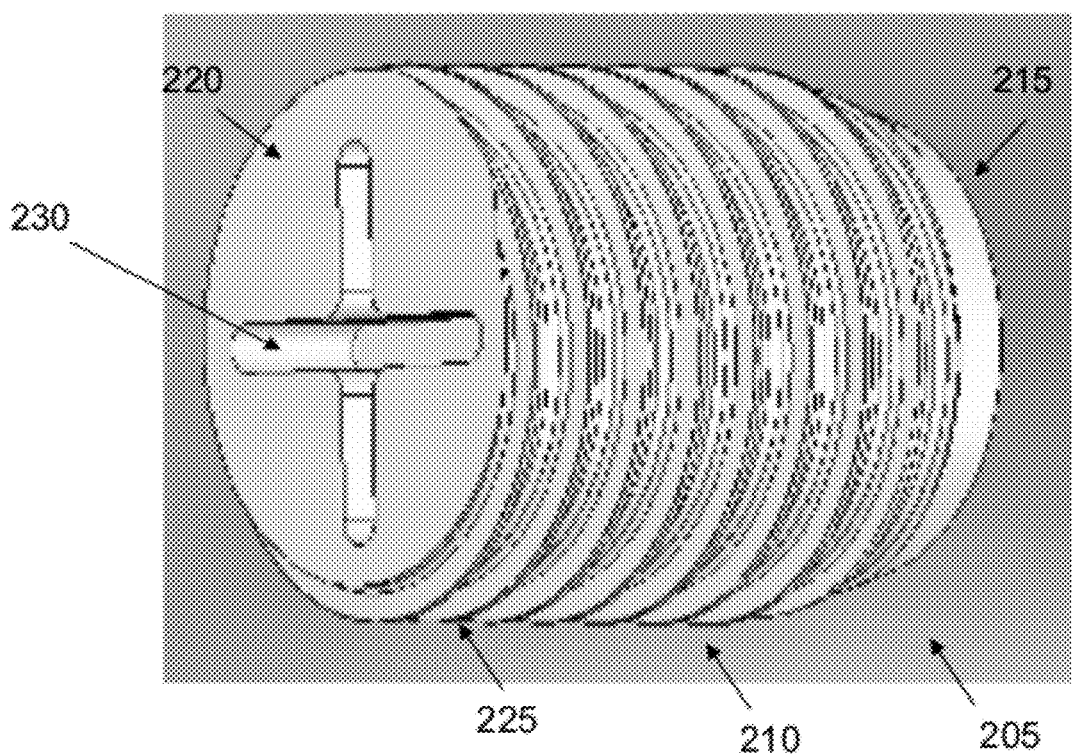
FIGS. 8 and 9 are schematic views showing a second novel osteotomy implant formed in accordance with the present invention.
Figure 9:
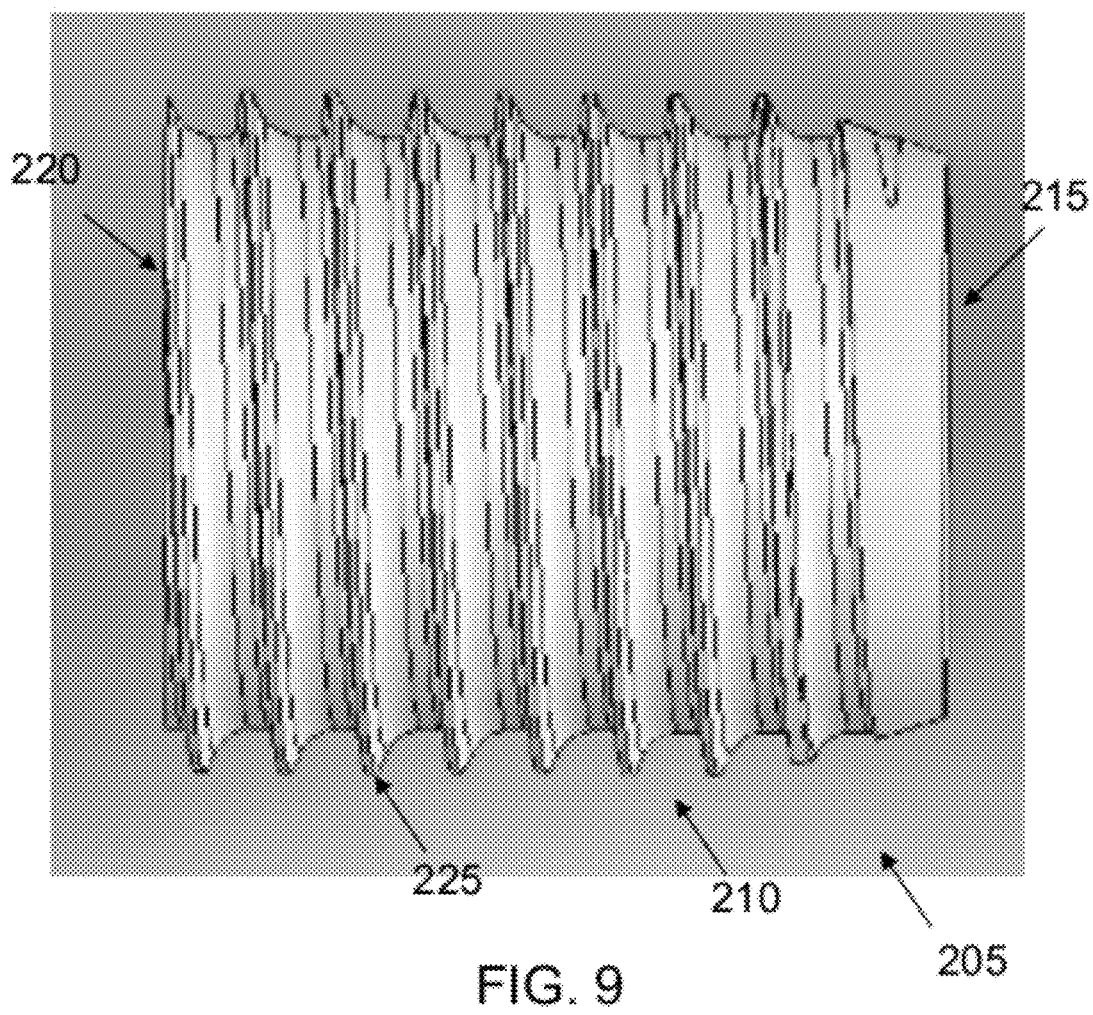

Looking next at FIGS. 6 and 7, osteotomy implant 105 is deployed in wedge-like opening W by fitting an appropriate driver (not shown) into recess 130, placing the distal end of osteotomy implant 105 into bore B, and then turning osteotomy implant 105 with the driver so as to threadingly advance osteotomy implant 105 into wedge-like opening W. As this occurs, threads 125 engage the bone on either side of wedge-like opening W and stabilize the bone portions in position relative to the osteotomy implant and, hence, in position relative to one another.

In this respect it will be appreciated that, by forming osteotomy implant 105 with a tapered configuration, insertion of osteotomy implant 105 into bore B is facilitated.

Significantly, as osteotomy implant 105 advances into bore B, it effectively "jacks open" wedge-like opening W, since the proximal end of osteotomy implant 105 is oversized relative to bore B. Thus, a surgeon can achieve a desired degree of correction simply by advancing osteotomy implant 105 an appropriate distance into wedge-like opening W. As a result, a single size of osteotomy implant 105 can be used effectively on a wide range of different anatomy sizes to achieve a wide range of different angle corrections.

If desired, bore B may be omitted entirely, and osteotomy implant 105 inserted directly into wedge-like opening W, with screw threads 125 of the osteotomy implant engaging the adjacent bone surfaces.

Looking next at FIGS. 8-11, there is shown a second novel osteotomy implant 205 formed in accordance with the present invention. Osteotomy implant 205 is generally similar to osteotomy implant 105 in that it also comprises an elongated body 210 having a distal end 215 and a proximal end 220, and elongated body 210 comprises a screw thread 225 for engaging bone. However, with second osteotomy implant 205, elongated body 210 is not tapered, instead having the geometry of a threaded cylinder. However, the distal end of elongated body 210 is beveled so as to facilitate insertion into bore B (or, in the case where bore B is not provided, directly into wedge-like opening W). Furthermore, osteotomy implant 205 has its recess 230 in the form of a Philips-type geometry.

Figure 10:
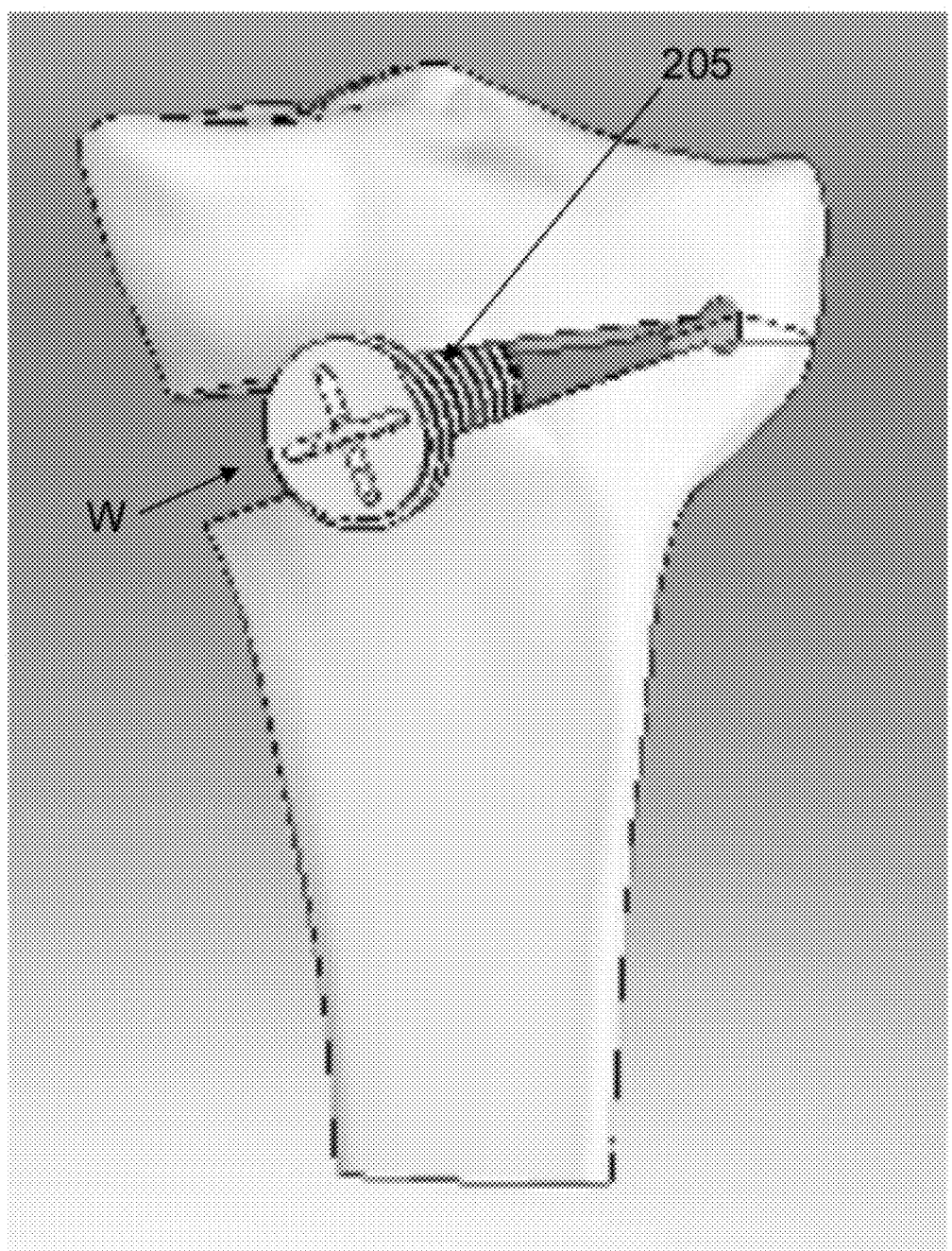
FIGS. 10 and 11 are schematic views showing the osteotomy implant of FIGS. 8 and 9 positioned within an osteotomy cut formed in the tibia.
Figure 11:
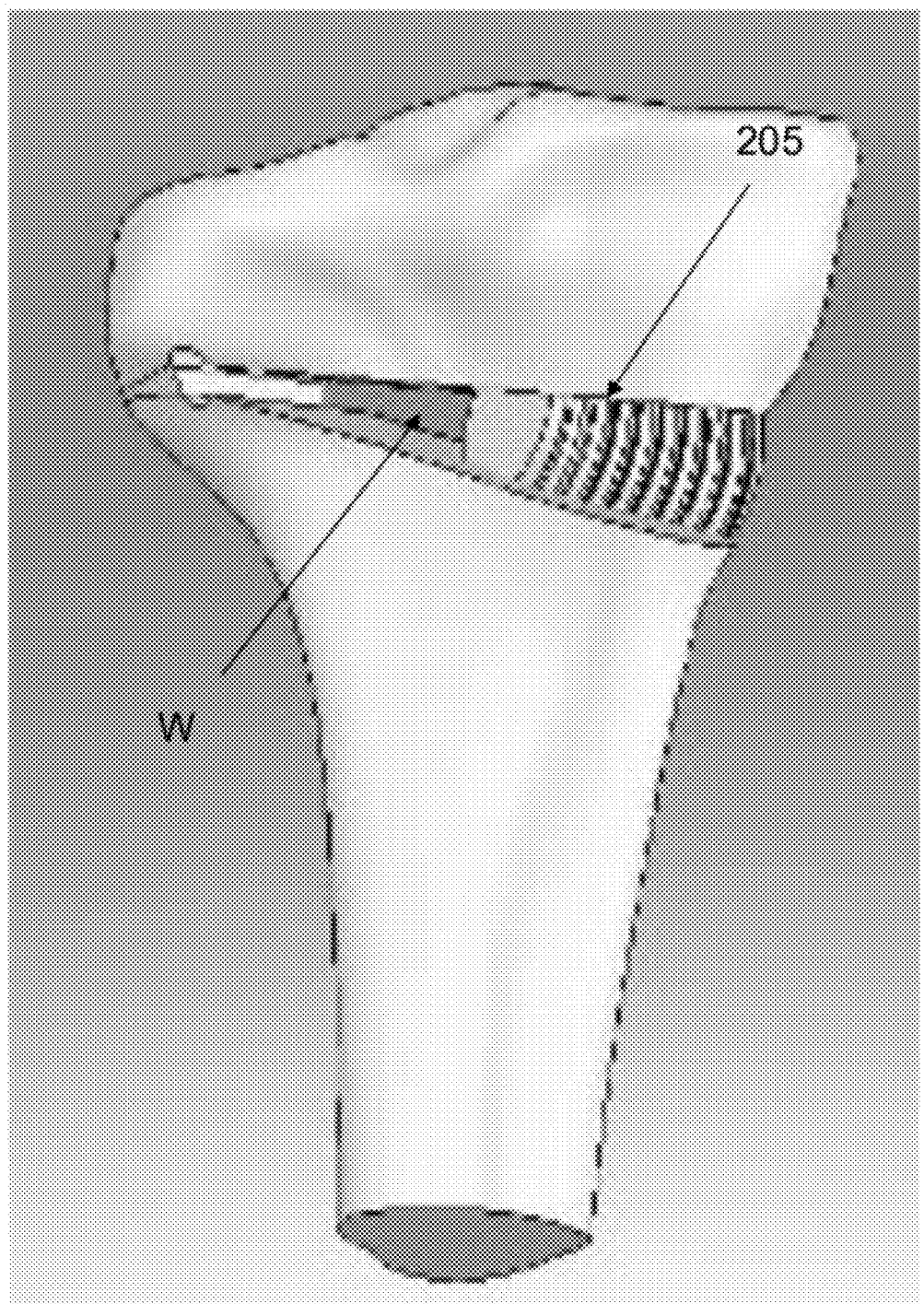
Figure 12:
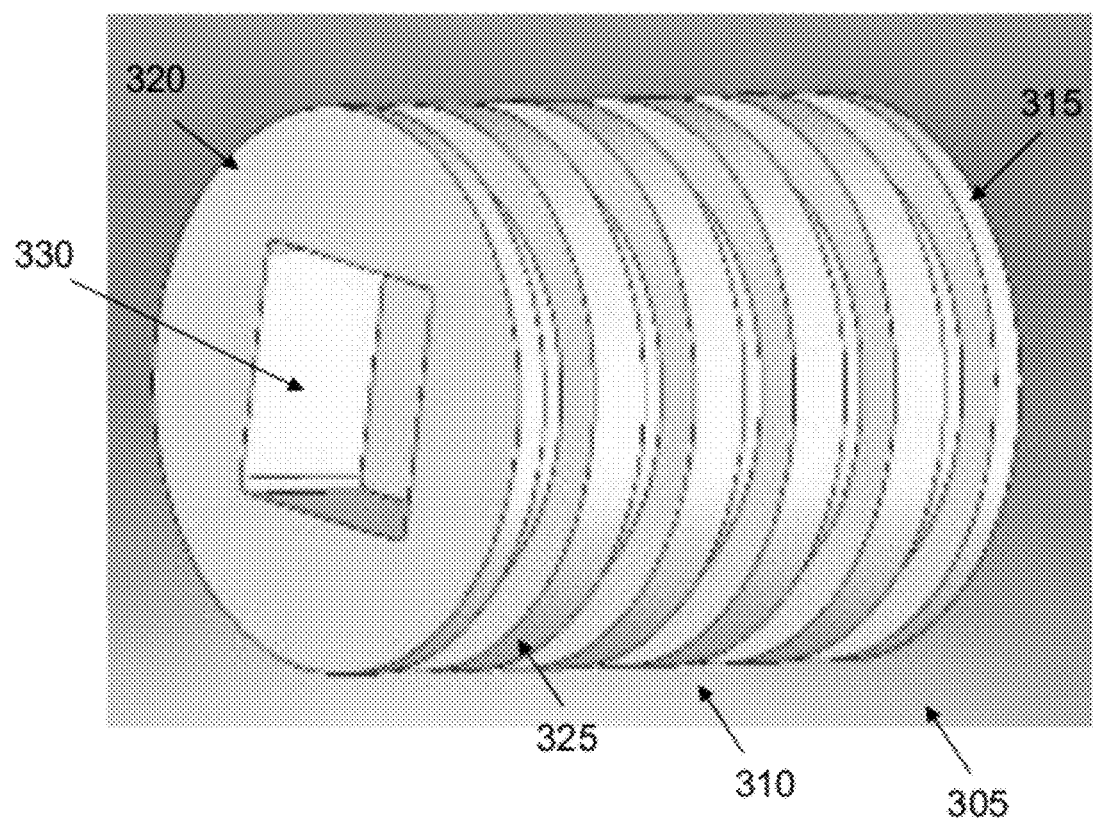
FIGS. 12 and 13 are schematic views showing a third novel osteotomy implant formed in accordance with the present invention.
Figure 13:
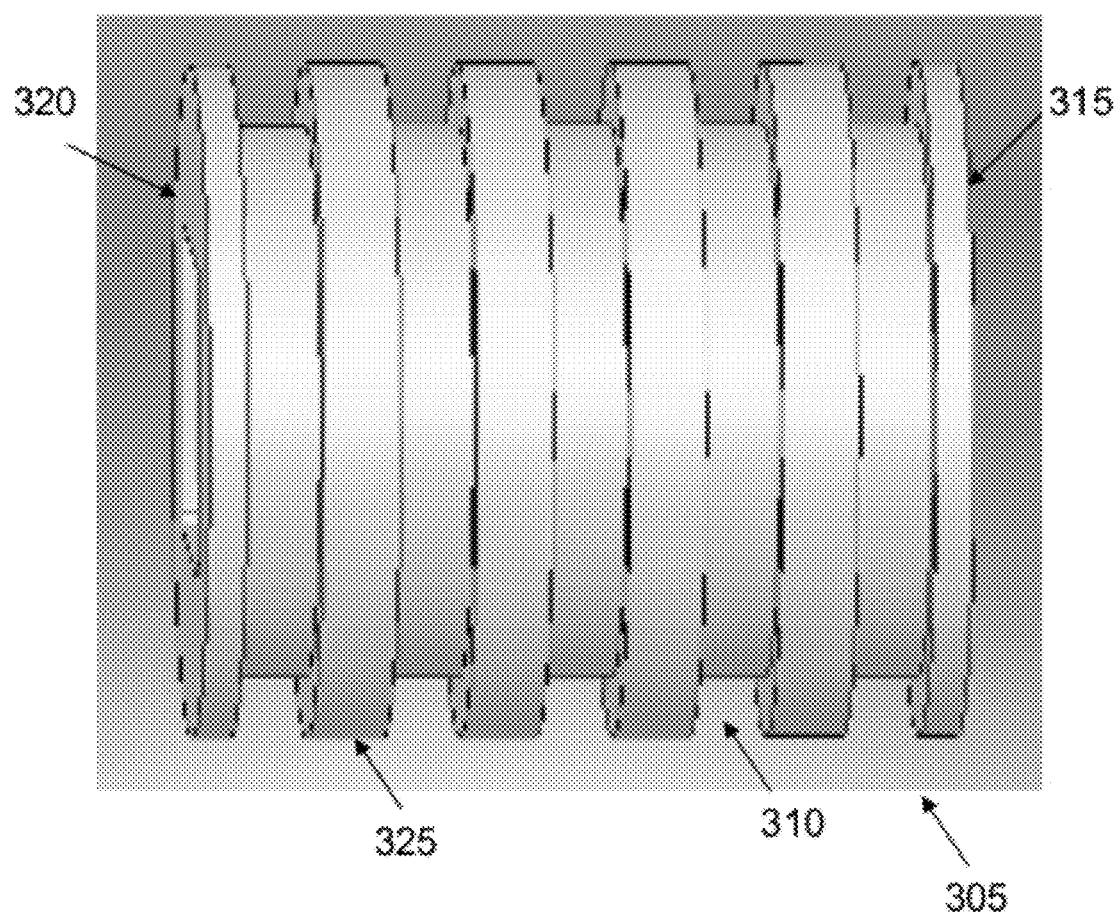
Figure 14:
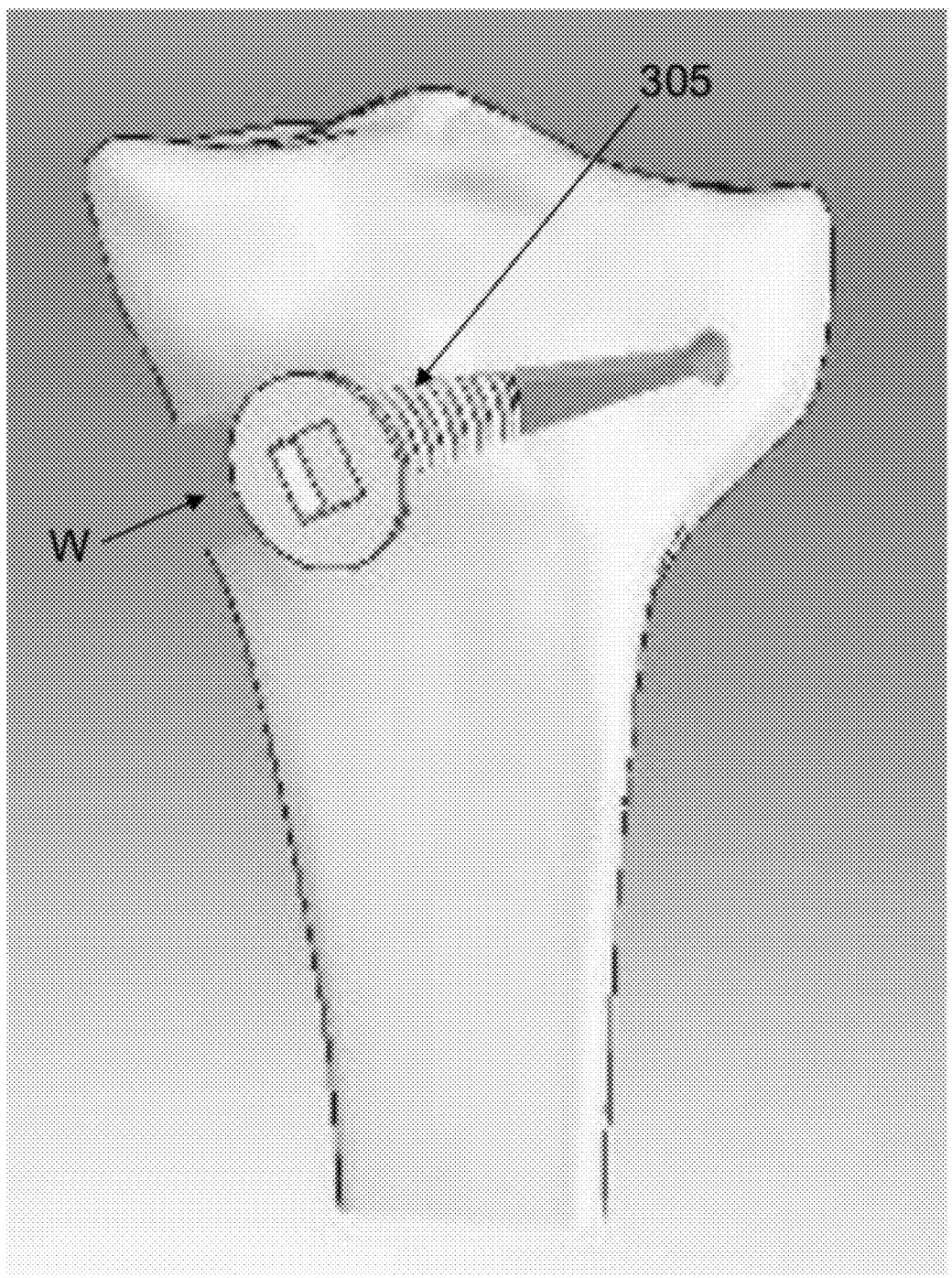
FIGS. 14 and 15 are schematic views showing the osteotomy implant of FIGS. 12 and 13 positioned within an osteotomy cut formed in the tibia.
Figure 15:
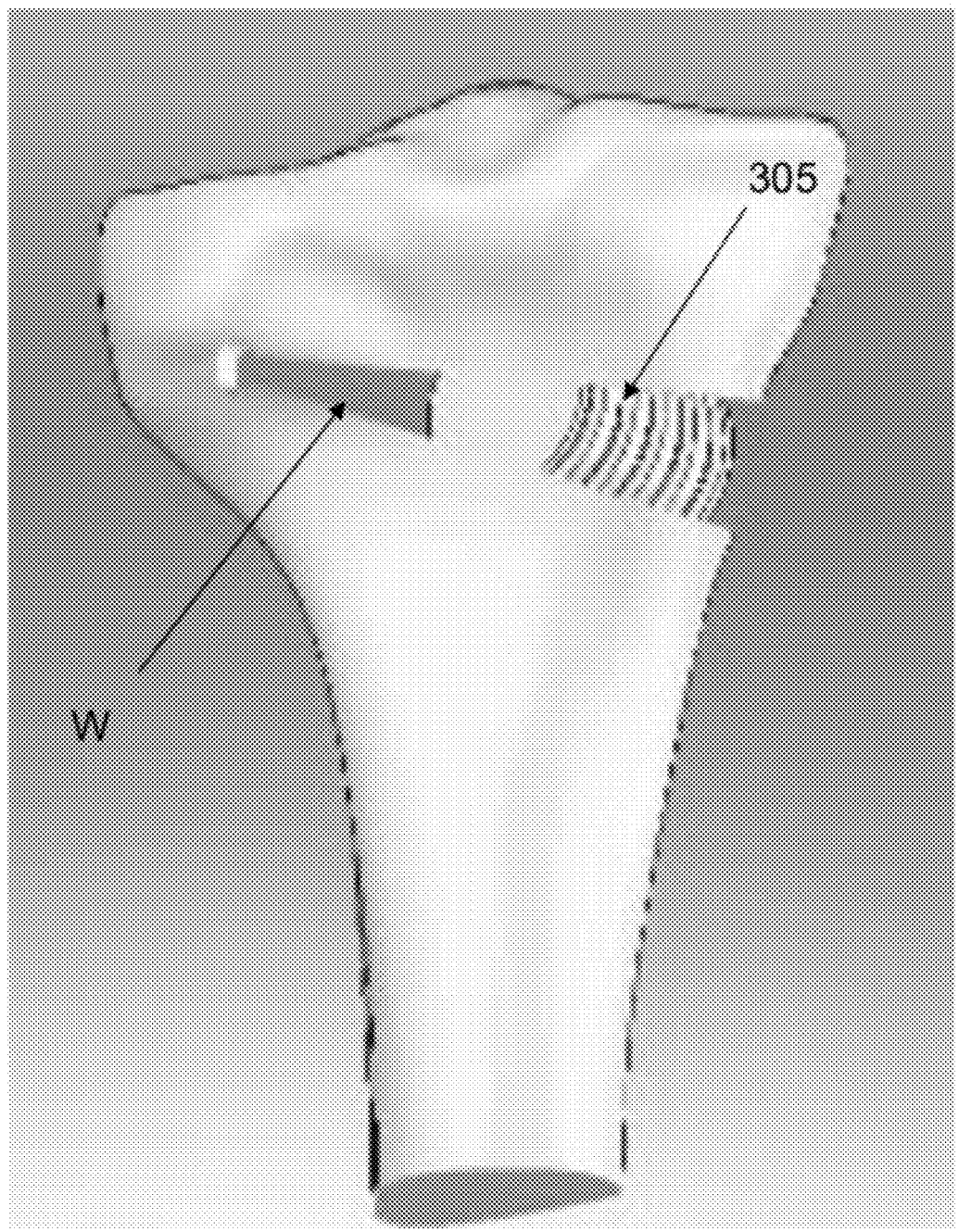
Figure 16:
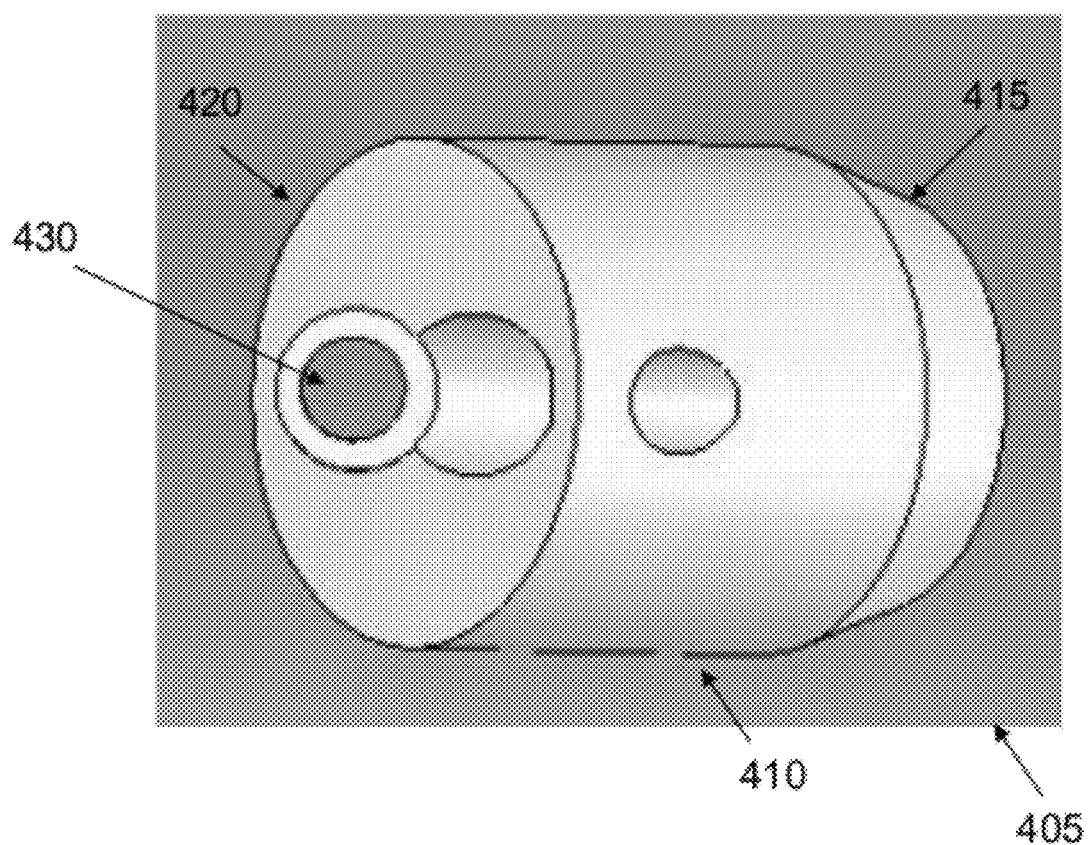
FIGS. 16 and 17 are schematic views showing a fourth novel osteotomy implant formed in accordance with the present invention.
Figure 17:
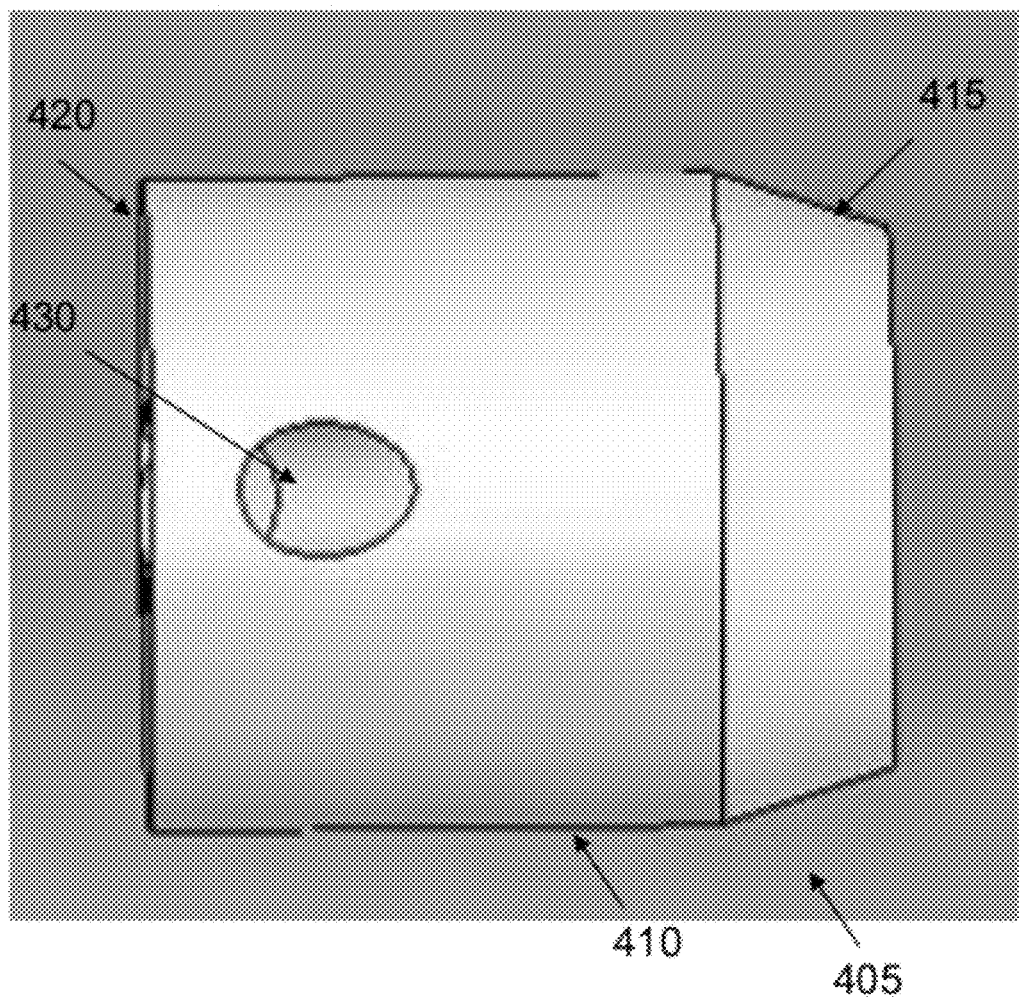
Figure 18:
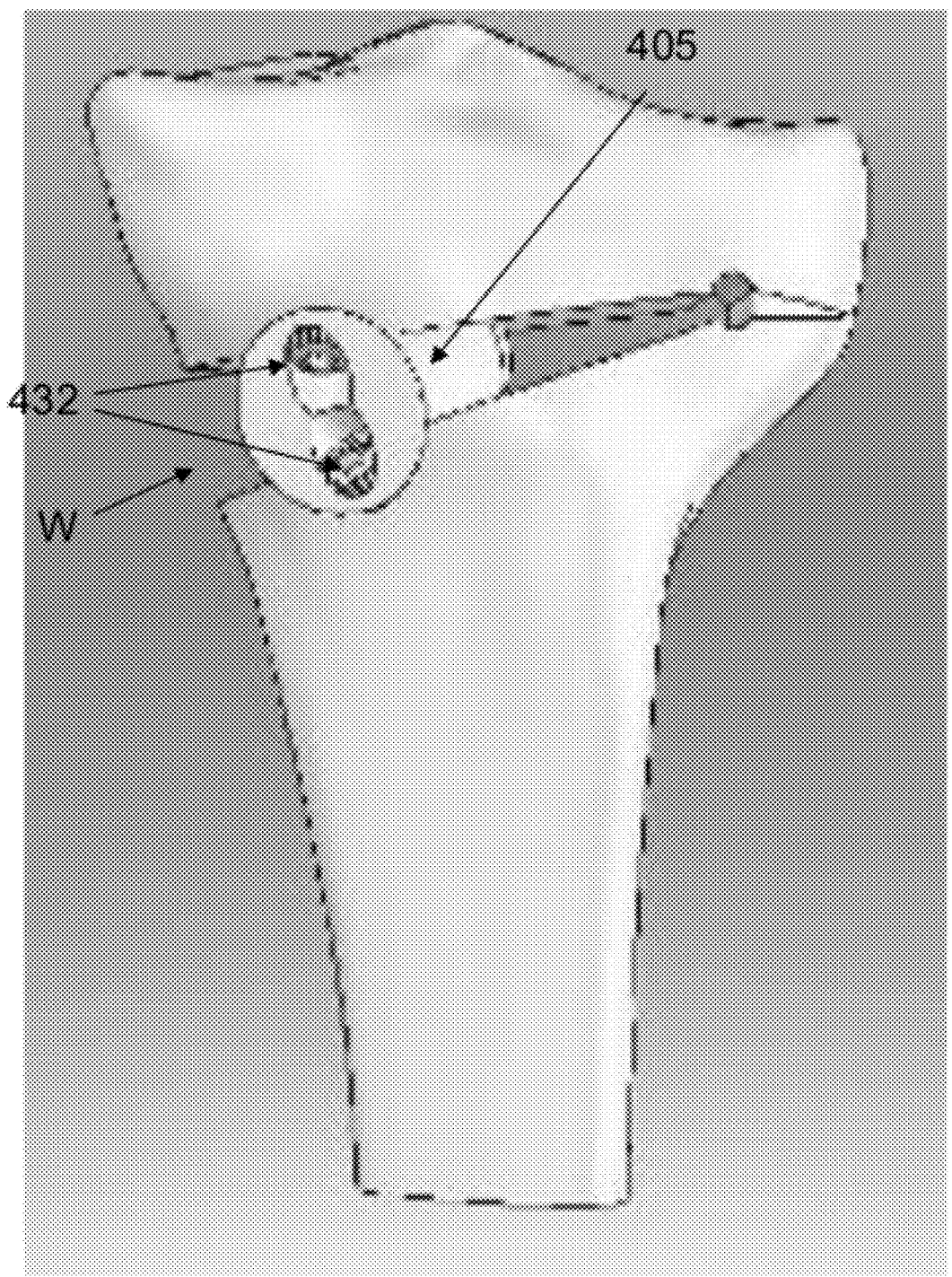
FIGS. 18 and 19 are schematic views showing the osteotomy implant of FIGS. 16 and 17 positioned within an osteotomy cut formed in the tibia.
Figure 19:
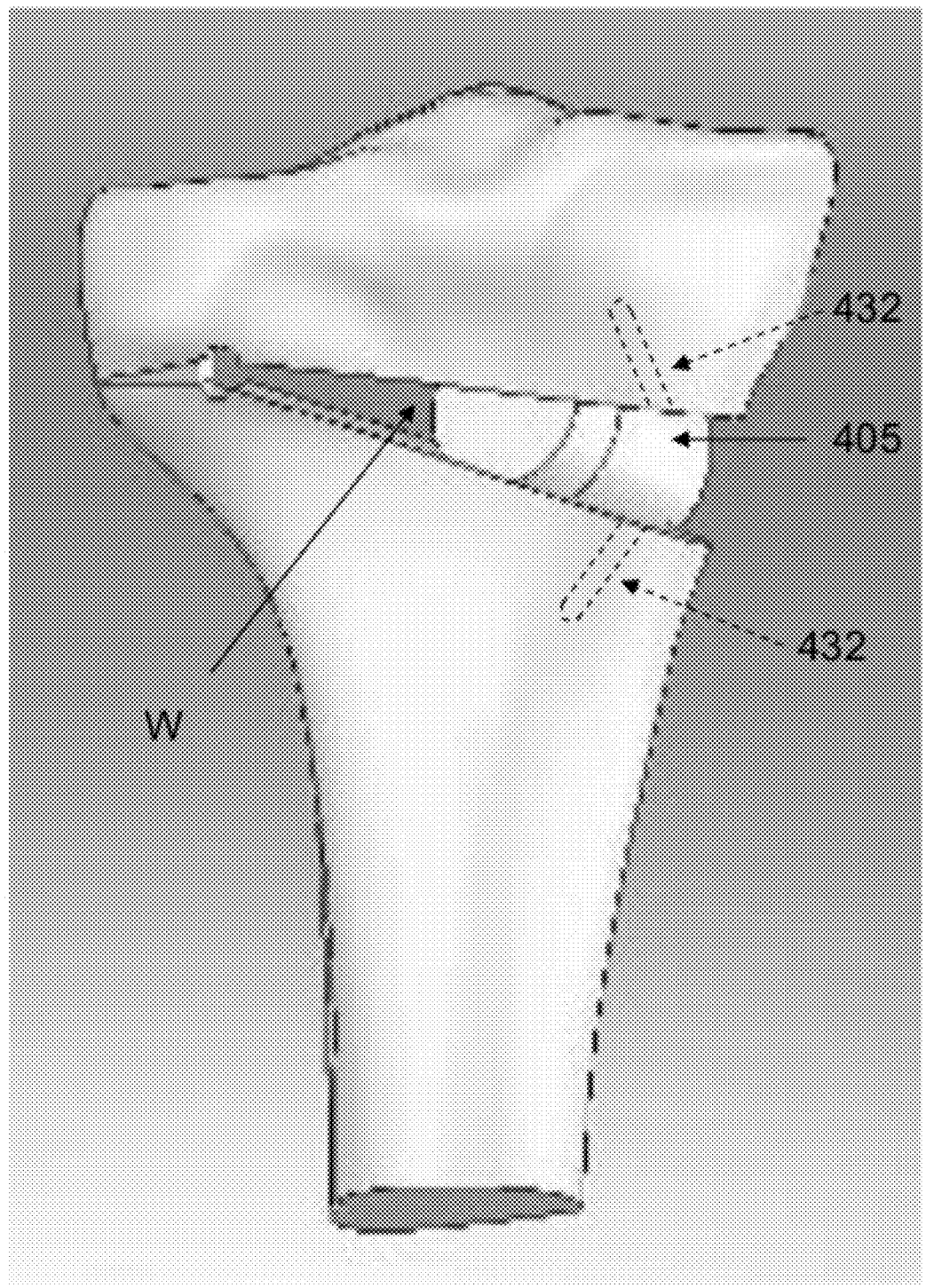

As shown in FIGS. 10-11, osteotomy implant 205 is used in a manner which is similar to that of osteotomy implant 105.

Looking next at FIGS. 12-15, there is shown a third novel osteotomy implant 305 formed in accordance with the present invention. Osteotomy implant 305 is generally similar to osteotomy implant 105 in that it also comprises an elongated body 310 having a distal end 315 and a proximal end 320. However, with third osteotomy implant 305, elongated body 310 is provided with ribs 325 instead of threads and, like osteotomy implant 205, is not tapered, instead having the geometry of a ribbed cylinder.

Osteotomy implant 305 is used in a manner which is similar to that of osteotomy implant 105, in the sense that it is advanced an appropriate distance into wedge-like opening W so as to stabilize the bone portions with the desired positioning. However, with osteotomy implant 305, the implant is deployed by driving it forward (e.g., by tapping with a hammer) into wedge-like opening W, rather than by rotatably advancing the implant via screw threads 125. Ribs 325 help stabilize osteotomy implant 305 against retraction out of wedge-like opening W and facilitate osteointegration of the osteotomy implant 305 with the surrounding bone.

Looking next at FIGS. 16-19, there is shown a fourth novel osteotomy implant 405 formed in accordance with the present invention. Osteotomy implant 405 is generally similar to osteotomy implant 105 in that it also comprises an elongated body 410 having a distal end 415 and a proximal end 420. However, with fourth osteotomy implant 405, elongated body 410 is not provided with threads or ribs and, like osteotomy implant 205, is not tapered. Instead, osteotomy implant 405 comprises a generally cylindrical body having a beveled distal end. Furthermore, elongated body 410 is provided with one or more crossbores 430 for receiving a toe screw or toe pin 432 (not shown in FIGS. 16 and 17, but shown in FIGS. 18 and 19) therethrough, for anchoring osteotomy implant 405 to the bone, as will hereinafter be discussed.

Osteotomy implant 405 is used in a manner which is similar to that of osteotomy implant 105, in the sense that it is advanced an appropriate distance into wedge-like opening W so as to stabilize the bone portions with the desired positioning. However, with osteotomy implant 405, the osteotomy implant is deployed by driving it forward into wedge-like opening W, rather than by rotatably advancing the implant via screw threads. Once osteotomy implant 405 has been inserted to the appropriate depth within wedge-like opening W, toe screw(s) or toe pin(s) 432 are passed through crossbore(s) 430 and into the adjacent bone. The provision of crossbore(s) 430 and toe screw(s) or toe pin(s) 432 help stabilize osteotomy implant 405 against retraction out of wedge-like opening W.

Figure 20:
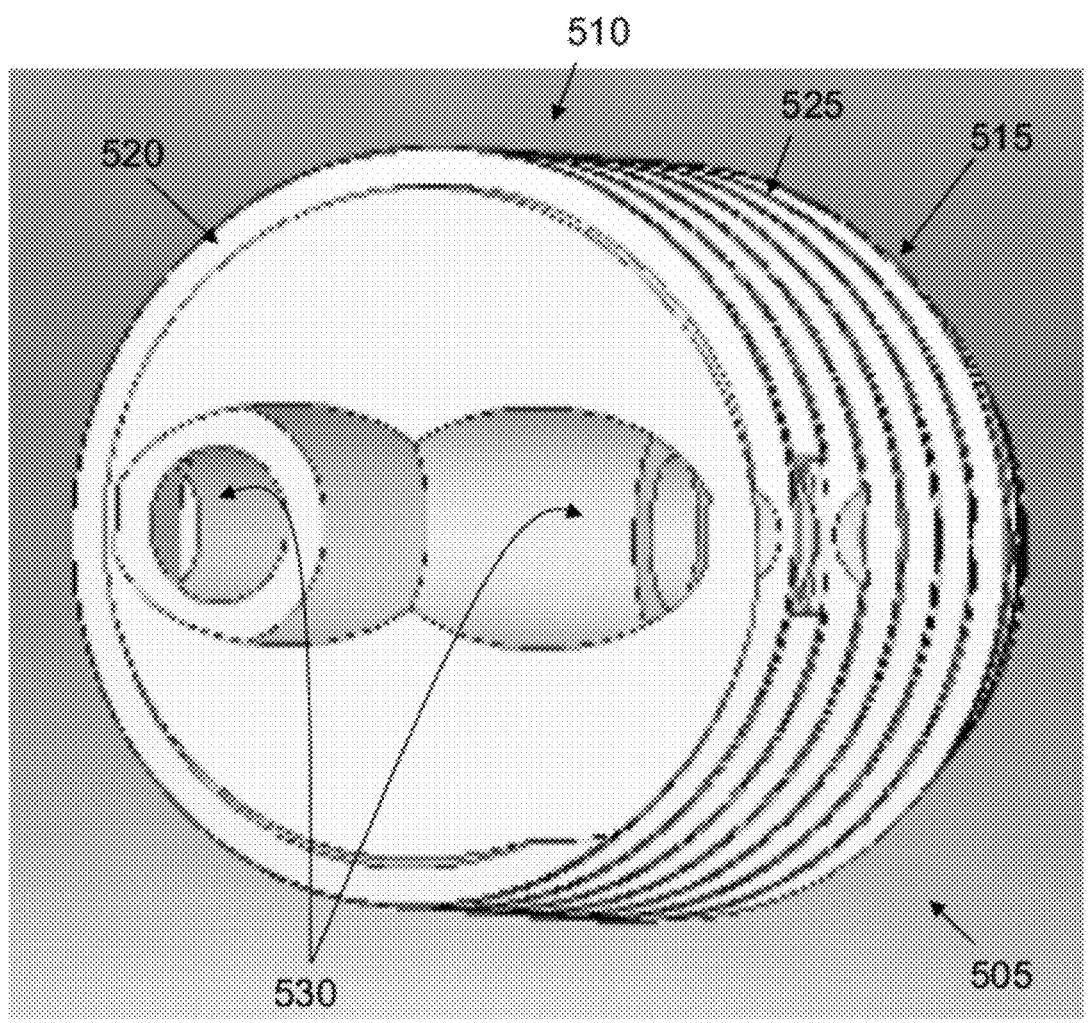
FIG. 20 is a schematic view showing a fifth novel osteotomy implant formed in accordance with the present invention.
Figure 21:
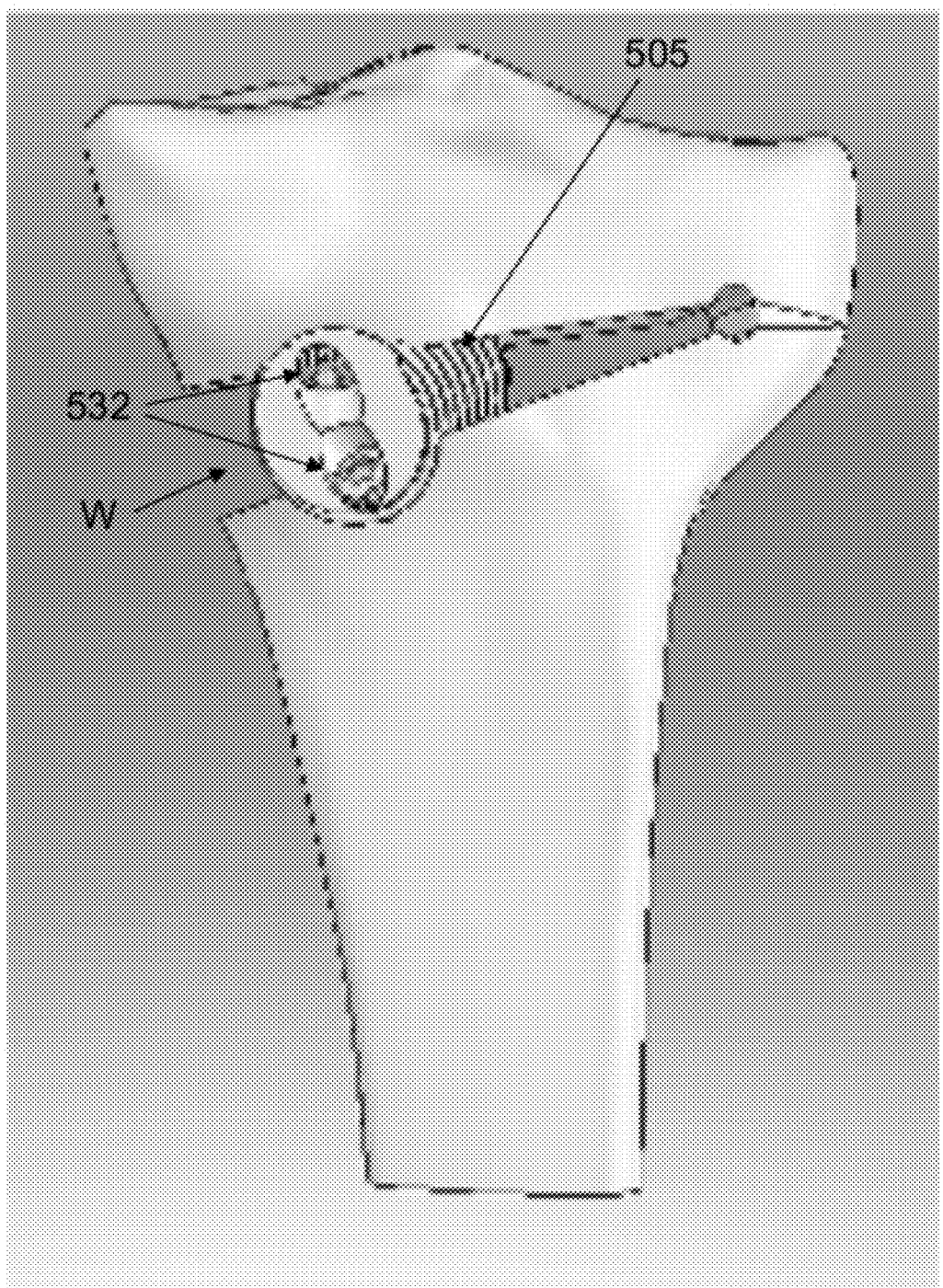
FIGS. 21 and 22 are schematic views showing the osteotomy implant of FIG. 20 positioned within an osteotomy cut formed in the tibia.
Figure 22:
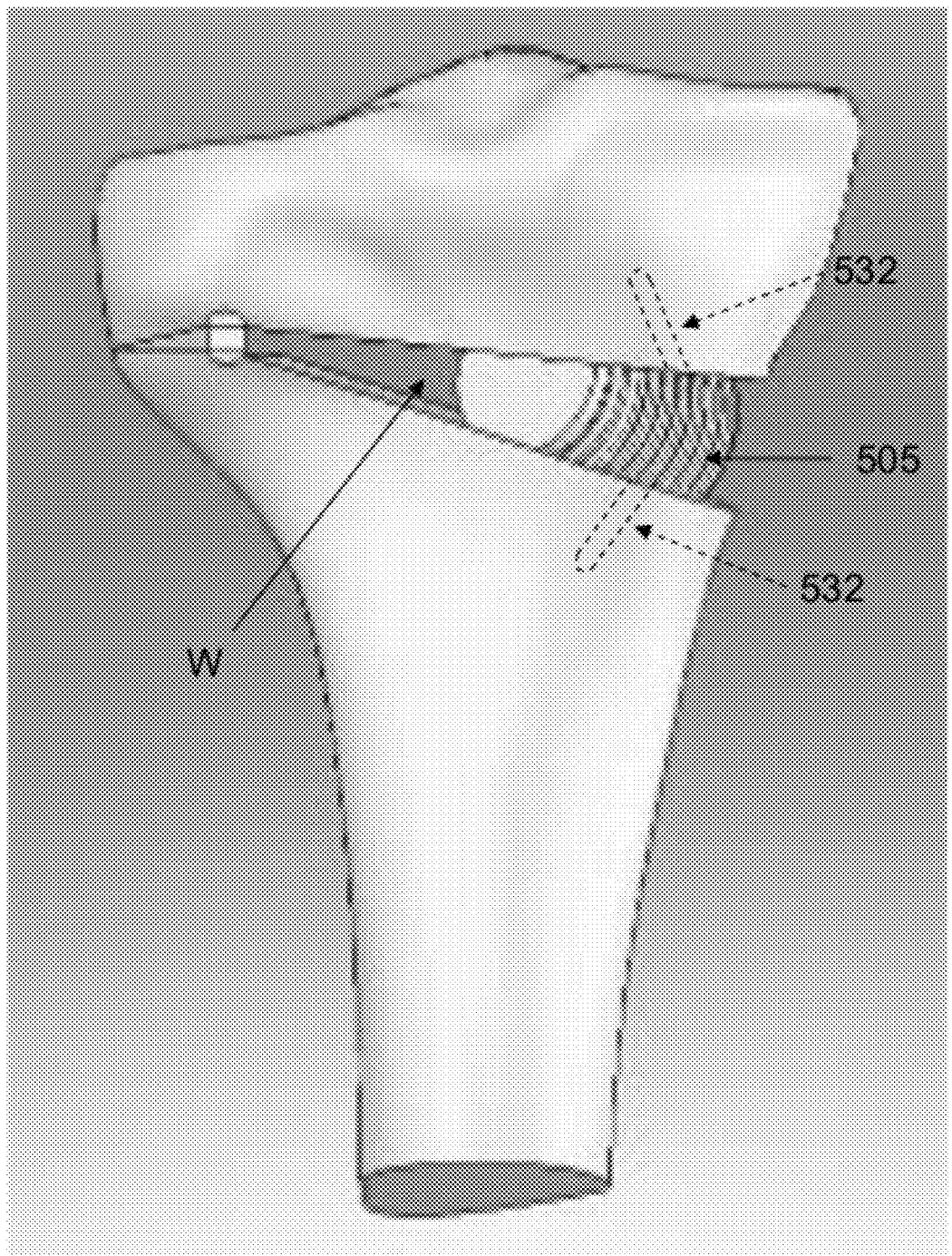
Figure 23:
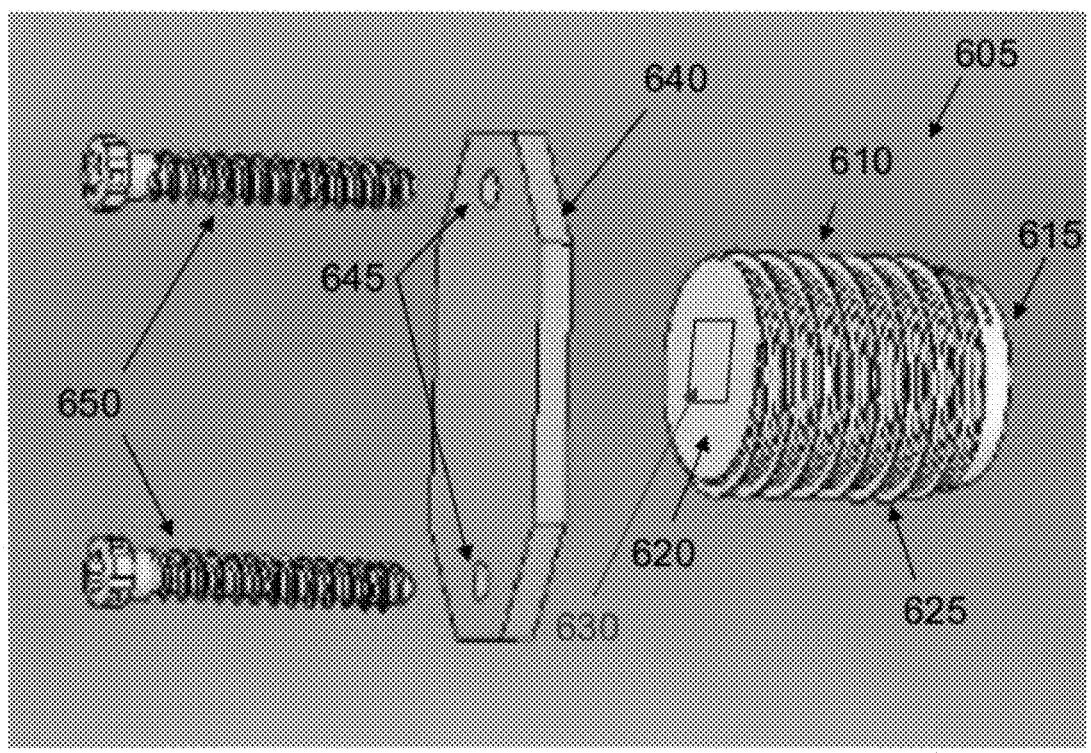
FIGS. 23 and 24 are schematic views showing a sixth osteotomy implant, including an osteotomy plate, formed in accordance with the present invention.
Figure 24:
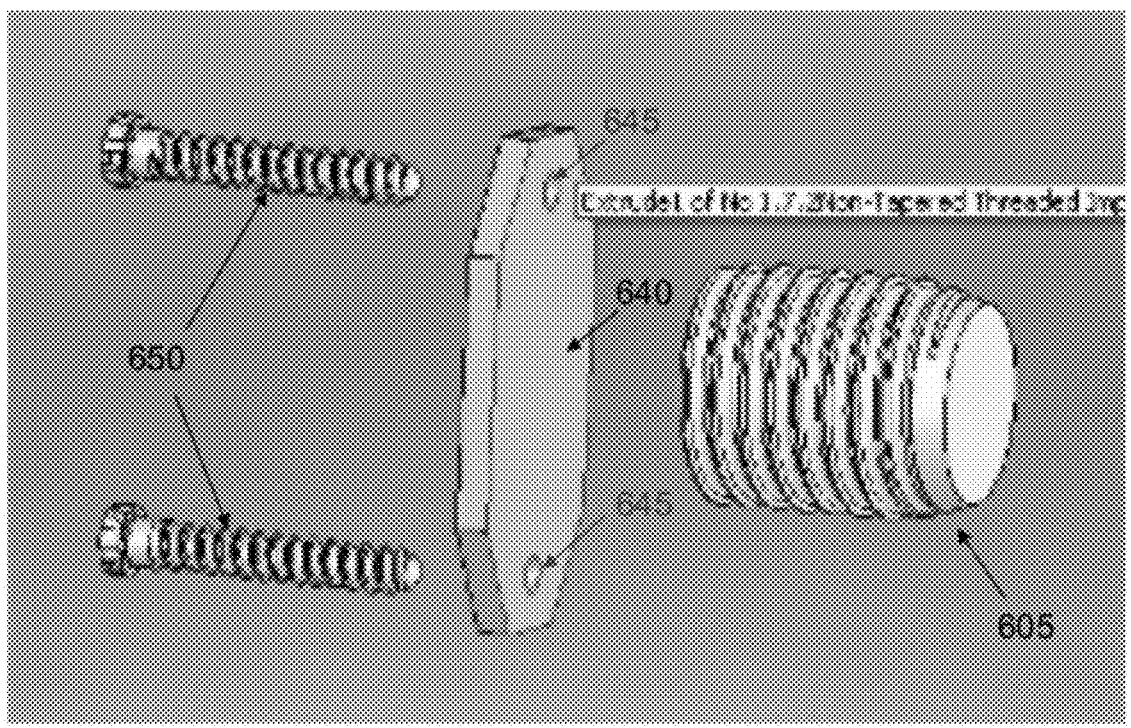
Figure 25:
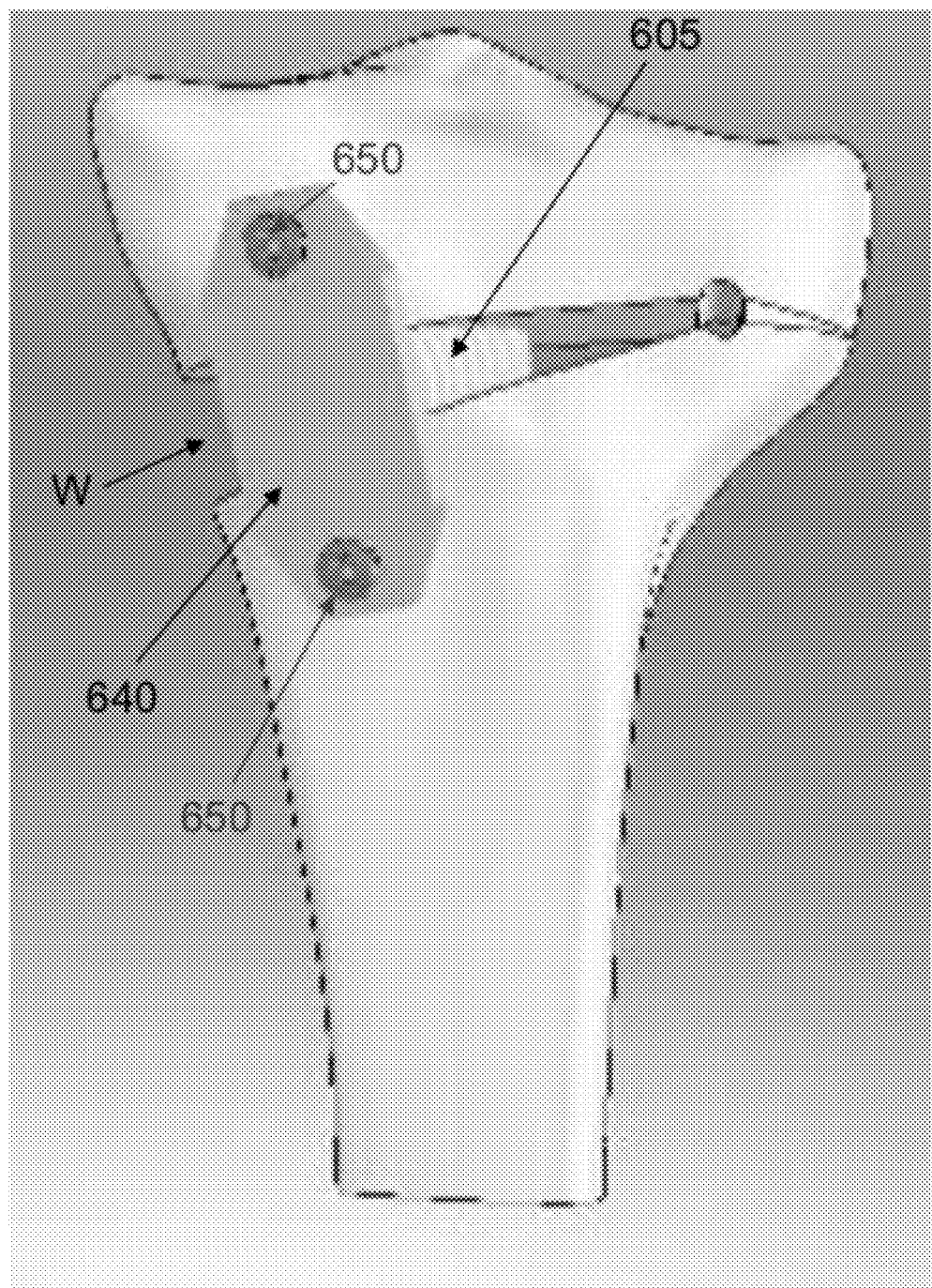
FIGS. 25 and 26 are schematic views showing the osteotomy implant and osteotomy plate of FIGS. 23 and 24 positioned within an osteotomy cut formed in the tibia.
Figure 26:
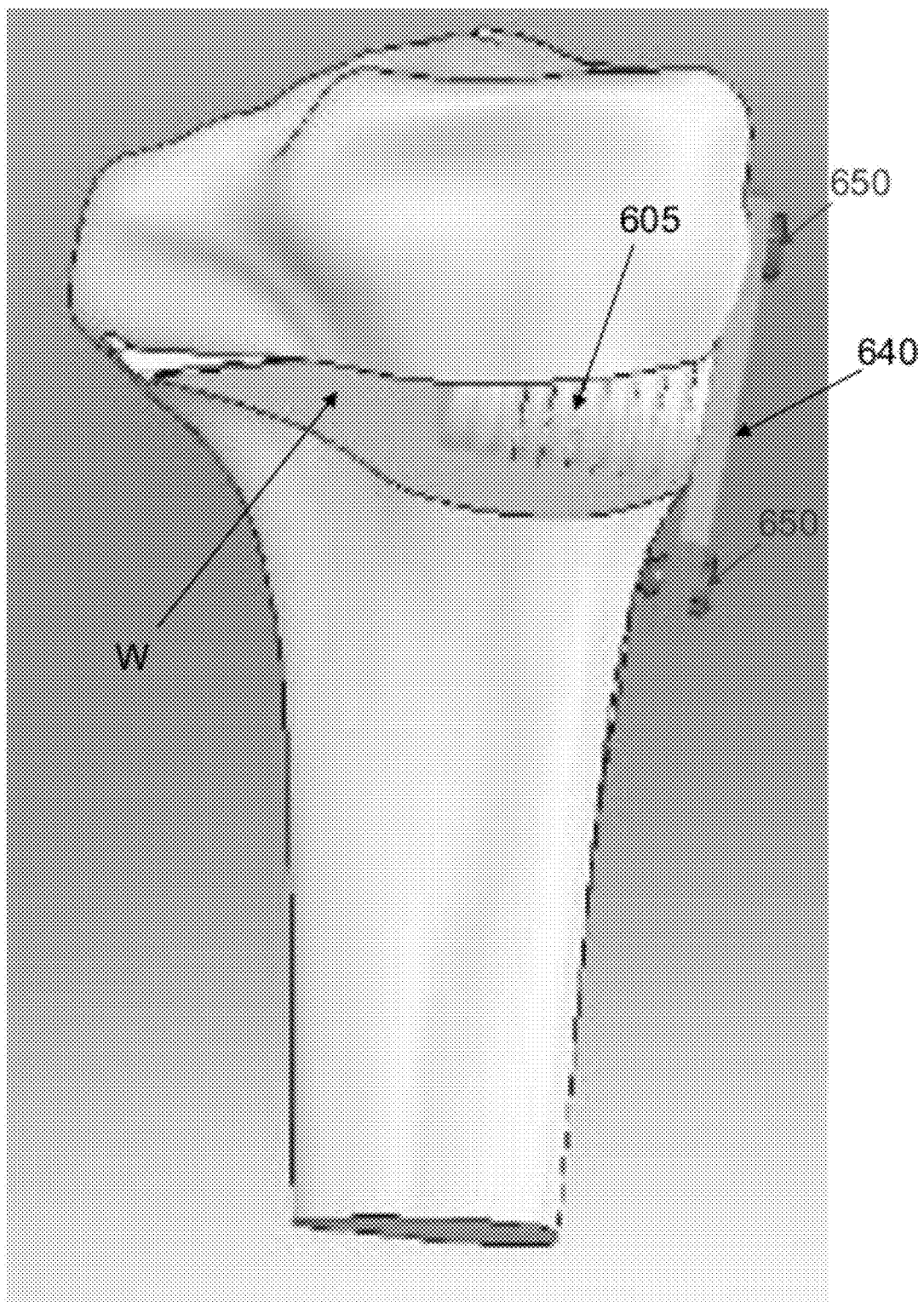

Looking next at FIGS. 20-22, there is shown a fifth novel osteotomy implant 505 formed in accordance with the present invention. Osteotomy implant 505 is generally similar to osteotomy implant 105 in that it also comprises an elongated body 510 having a distal end 515 and a proximal end 520, and elongated body comprises a screw thread 525. However, with fifth osteotomy implant 505, elongated body 510 is provided with one or more crossbore(s) 530 for receiving a toe screw or a toe pin 532 (not shown in FIG. 20, but shown in FIGS. 21 and 22) therethrough, for anchoring osteotomy implant 505 to the bone, as will hereinafter be discussed.

Osteotomy implant 505 is used in a manner which is similar to that of osteotomy implant 105, in the sense that it is advanced an appropriate distance into wedge-like opening W so as to stabilize the bone portions with the desired positioning. However, unlike osteotomy implant 105, when osteotomy implant 505 has been advanced an appropriate distance within wedge-like opening W, toe screw(s) or toe pin(s) 532 are passed through crossbore(s) 530 and into the adjacent bone. The provision of crossbore(s) 530 and toe screw(s) or toe pin(s) 532 help stabilize osteotomy implant 505 against retraction out of wedge-like opening W.

Looking next at FIGS. 23-26, there is shown a sixth novel osteotomy implant 605 formed in accordance with the present invention. Osteotomy implant 605 is generally similar to osteotomy implant 105 in that it also comprises an elongated body 610 having a distal end 615 and a proximal end 620, and elongated body 610 comprises a screw thread 625 for engaging bone. However, osteotomy implant 605 also includes the provision of an osteotomy plate 640 for securing to the exterior surface of the bone adjacent to wedge-like opening W, in order to "cap" the opening and prevent osteotomy implant 605 from retracting out of wedge-like opening W. Osteotomy plate 640 is provided with two screw holes 645 extending therethrough for receiving bone screws 650.

Osteotomy implant 605 is used in a manner which is similar to that of osteotomy implant 105 except, however, after osteotomy implant 605 has been advanced an appropriate distance within wedge-like opening W, osteotomy plate 640 is positioned along the exterior surface of the bone, adjacent to wedge-like opening W. It should be appreciated that in some instances, osteotomy plate 640 will directly engage the proximal end of osteotomy implant 605. In other instances, osteotomy implant 605 may be advanced so far into wedge-like opening W as to prevent osteotomy plate 640 from directly engaging osteotomy implant 605. In either case, osteotomy plate 640 is then secured to the exterior surface of the bone adjacent wedge-like opening W using bone screws 650. The provision of osteotomy plate 640 and bone screws 650 help stabilize osteotomy implant 605 against retraction out of wedge-like opening W. In addition osteotomy plate 640 can also help carry load between the two bone portions.

It should be appreciated that bone screws 650 may be configured to advance directly into virgin bone or, if desired, bores for receiving bone screws 650 may be pre-drilled into the bone.

Figure 27:
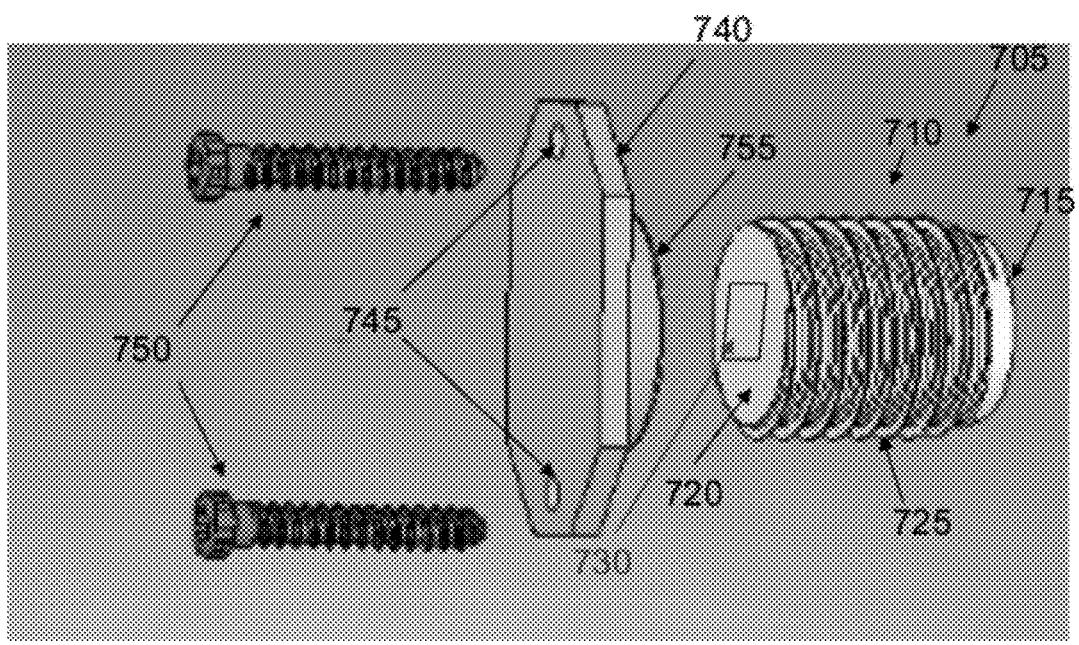
FIGS. 27 and 28 are schematic views showing a seventh osteotomy implant, including an osteotomy plate, formed in accordance with the present invention.
Figure 28:
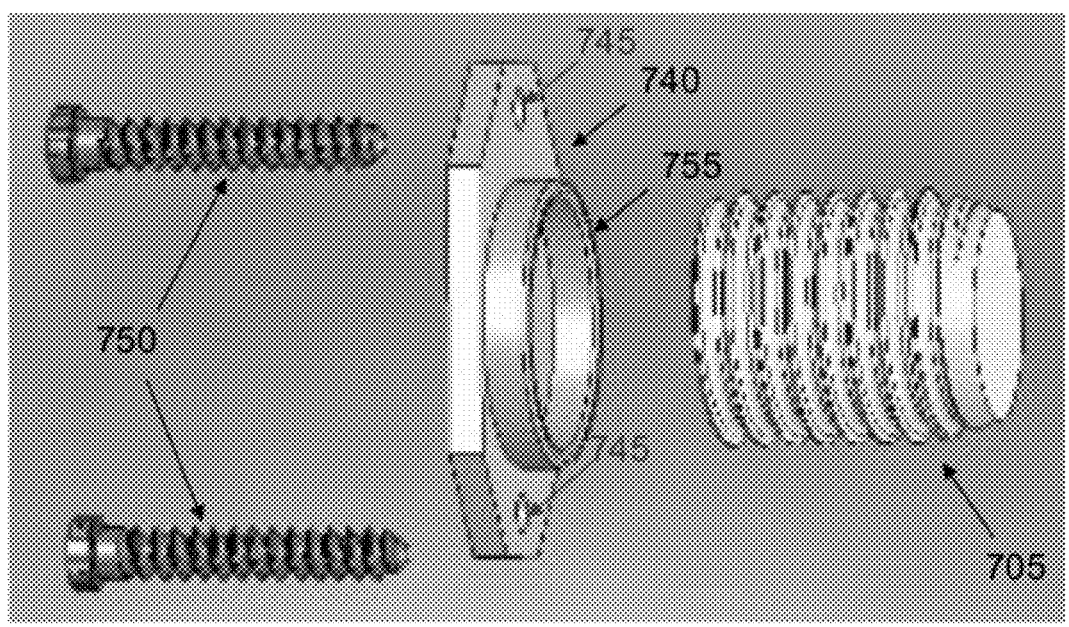
Figure 29:
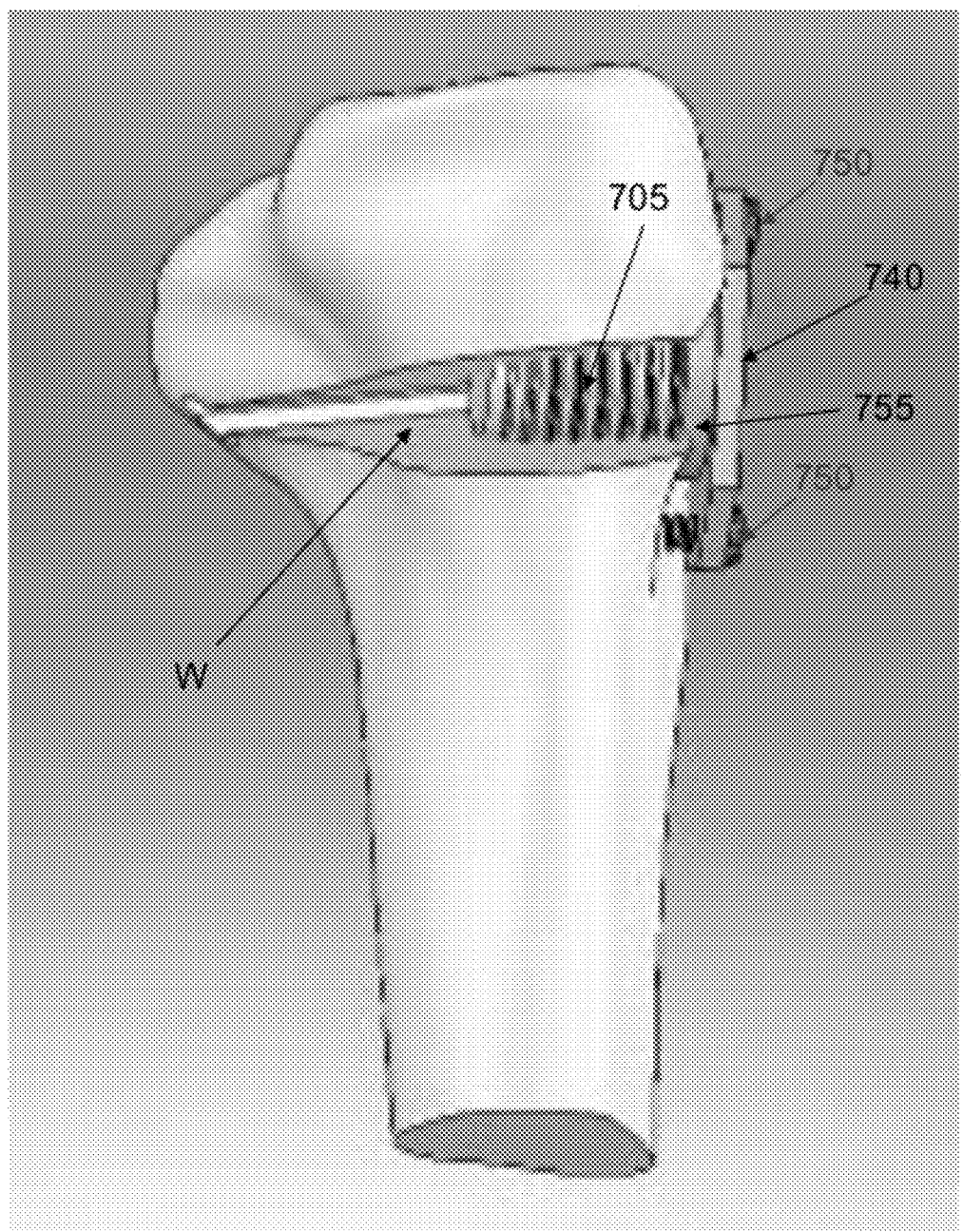
FIG. 29 is a schematic view showing the osteotomy implant and osteotomy plate of FIGS. 27 and 28 positioned within an osteotomy cut formed in the tibia.

Looking next at FIGS. 27-29, there is shown a seventh novel osteotomy implant 705 formed in accordance with the present invention. Osteotomy implant 705 is generally similar to osteotomy implant 605 in that it comprises an elongated body 710 having a distal end 715 and a proximal end 720, and elongated body 710 comprises a screw thread 725 for engaging bone. Also, like osteotomy implant 605, osteotomy implant 705 includes the provision of an osteotomy plate 740 for securing to the exterior surface of the bone adjacent to wedge-like opening W, in order to "cap" the opening and prevent osteotomy implant 705 from retracting out of wedge-like opening W. Osteotomy plate 740 is generally similar to osteotomy plate 640 in that it comprises a planar structure which is provided with two screw holes 745 extending therethrough for receiving bone screws 750. However, osteotomy plate 750 also comprises a rim 755 on its distal face for receiving the proximal end of osteotomy implant 705, as will hereinafter be discussed.

Osteotomy implant 705 is used in a manner which is similar to that of osteotomy implant 105. Once osteotomy implant 705 has been inserted to the appropriate depth within wedge-like opening W, osteotomy plate 740 is positioned against the exterior surface of the bone adjacent the wedge-like opening W, with rim 755 extending into wedge-like opening W. It should be appreciated that in some instances, osteotomy plate 740 will directly engage the proximal end of osteotomy implant 705, with rim 755 receiving the proximal end of osteotomy implant 705. In other instances, osteotomy implant 705 may be advanced so far into wedge-like opening W as to prevent osteotomy plate 740 from directly engaging osteotomy implant 705. In either case, osteotomy plate 740 is then secured to the exterior surface of the bone adjacent wedge-like opening W using bone screws 750. The provision of osteotomy plate 740 (with rim 755) and bone screws 750 help stabilize osteotomy implant 705 against retraction out of wedge-like opening W. In addition osteotomy plate 740 can also help carry load between the two bone portions.

It should be appreciated that osteotomy plate 740 may also be used in conjunction with a ribbed implant, such as implant 205, etc.

Figure 30:
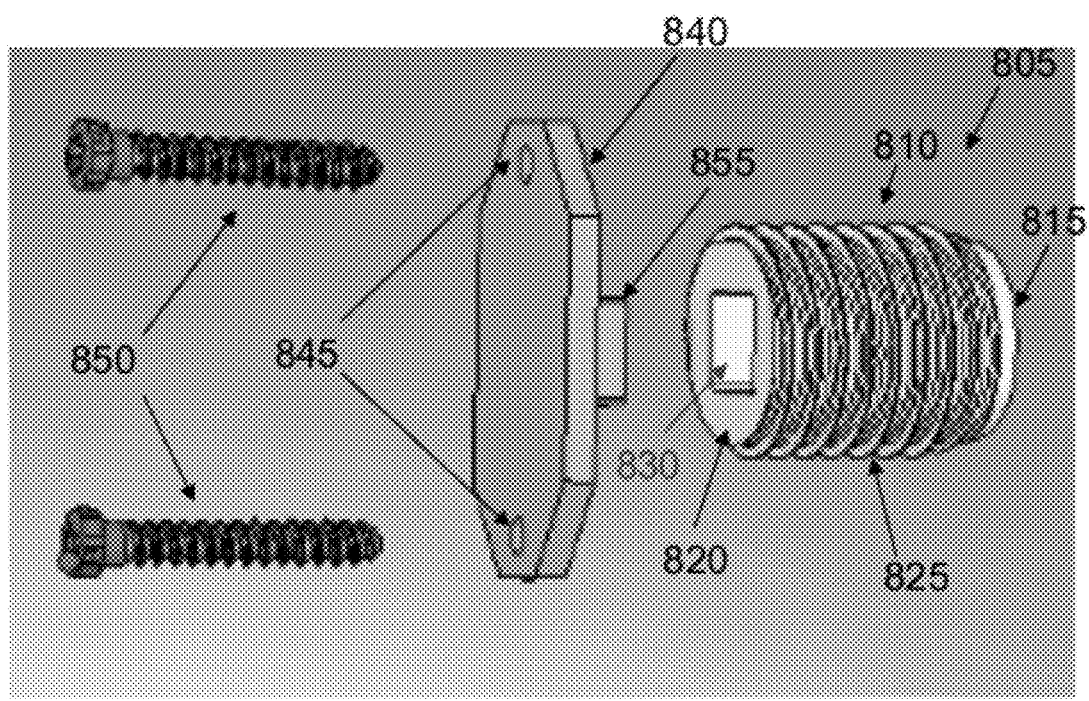
FIGS. 30 and 31 are schematic views showing an eighth novel osteotomy implant, including an osteotomy plate, formed in accordance with the present invention.
Figure 31:
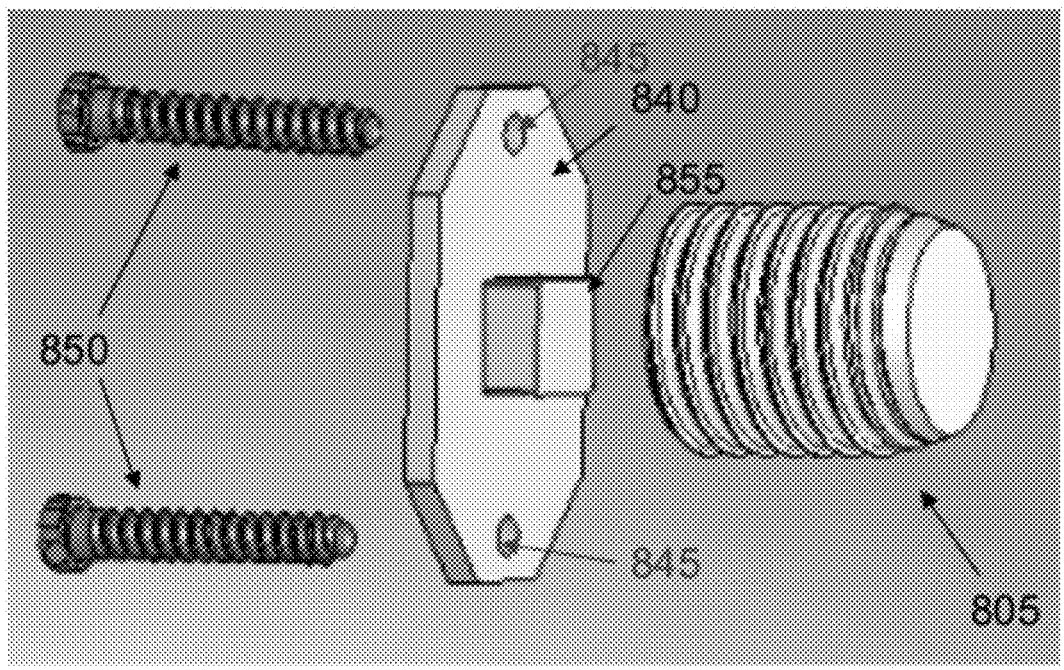

Looking next at FIGS. 30 and 31, there is shown an eighth novel osteotomy implant 805 formed in accordance with the present invention. Osteotomy implant 805 is generally similar to osteotomy implant 705 in that it comprises an elongated body 810 having a distal end 815 and a proximal end 820, and elongated body 810 comprises a screw thread 825 for engaging bone. Also, like osteotomy implant 705, osteotomy implant 805 includes the provision of an osteotomy plate 840. Osteotomy plate 840 is generally similar to osteotomy plate 740 in that it comprises a planar structure which is provided with two screw holes 845 extending therethrough for receiving bone screws 850. However, in place of rim 755, osteotomy plate 840 comprises a projection 855 for mating with recess 830 formed in the proximal end of osteotomy implant 805, as will hereinafter be discussed.

Osteotomy implant 805 is used in a manner which is similar to that of osteotomy implant 105. Once osteotomy implant 805 has been inserted to the appropriate depth within wedge-like opening W, osteotomy plate 840 is positioned against the exterior of wedge-like opening W with projection 855 seated in recess 830 formed in the proximal end of implant 805. Osteotomy plate 840 is then secured to the bone in a manner similar to that of osteotomy plate 740. The provision of osteotomy plate 840 (with rim 855) and bone screws 850 help stabilize osteotomy implant 805 against retraction out of wedge-like opening W. In addition osteotomy plate 840 can also help carry load between the two bone portions.

It should be appreciated that osteotomy plate 840 may also be used in conjunction with a ribbed implant, such as implant 205, etc.

Figure 32:
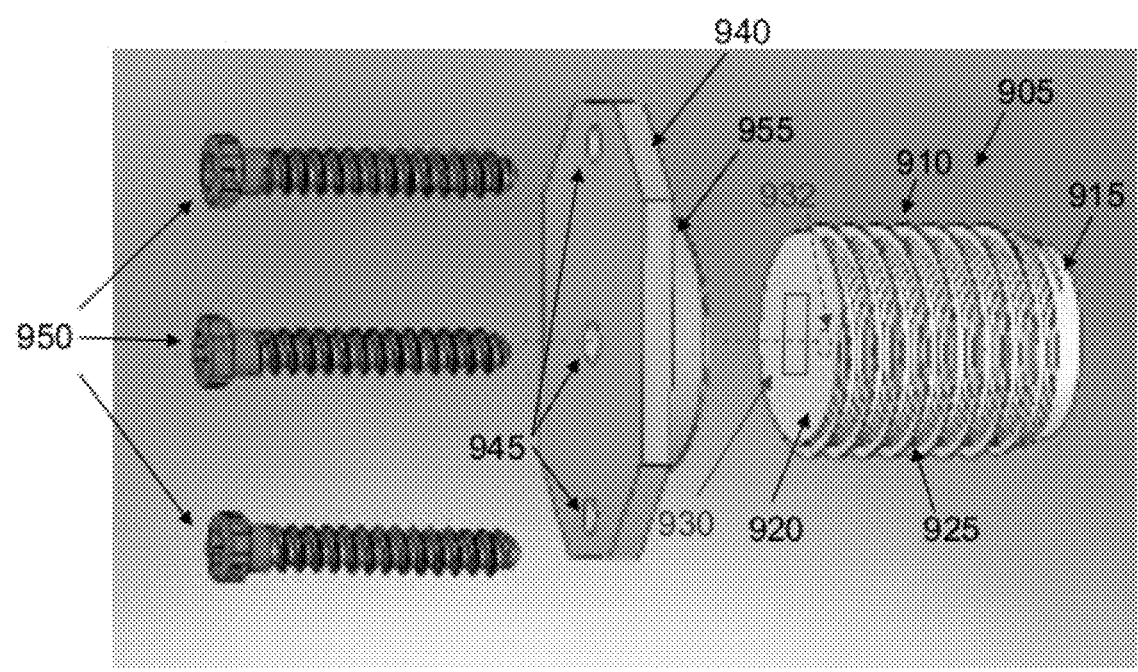
FIG. 32 is a schematic view showing a ninth novel osteotomy implant, including an osteotomy plate, formed in accordance with the present invention.
Figure 33:
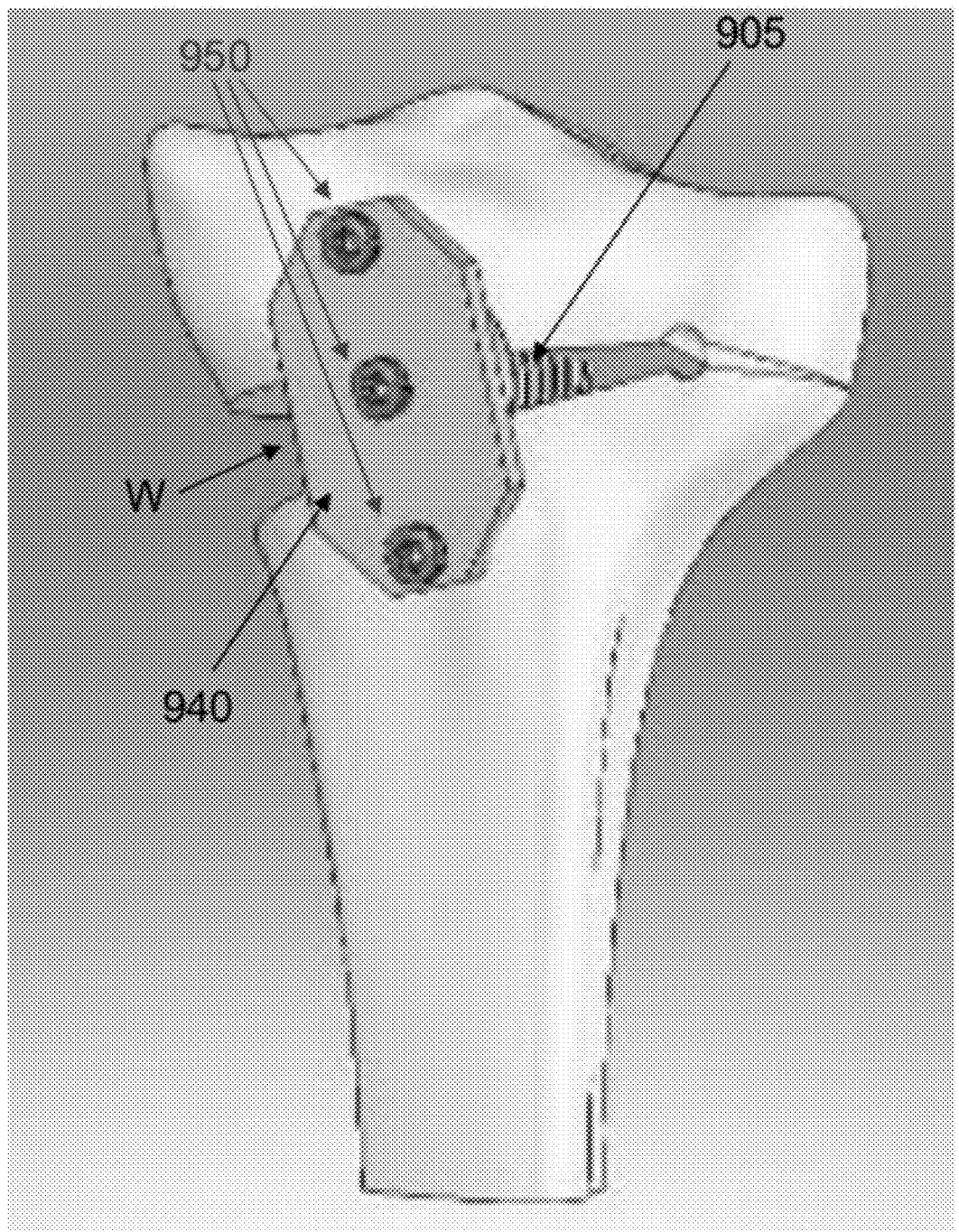
FIG. 33 is a schematic view showing the implant and osteotomy plate of FIG. 32 positioned within an osteotomy cut formed in the tibia.

Looking next at FIGS. 32 and 33, there is shown a ninth novel osteotomy implant 905 formed in accordance with the present invention. Osteotomy implant 905 is similar to osteotomy implant 705 in that it comprises an elongated body 910 having a distal end 915 and a proximal end 920, and elongated body 910 comprises a screw thread 925 for engaging bone. Also, like osteotomy implant 705, osteotomy implant 905 includes the provision of an osteotomy plate 940. Osteotomy plate 940 is generally similar to osteotomy plate 740 in that it is provided with a rim 955 for mating with proximal end of osteotomy implant 905. However, osteotomy plate 940 is provided with three screw holes 945 extending therethrough in place of the two screw holes 745 formed in osteotomy plate 740, and three bone screws 950.

Osteomtomy implant 905 and osteotomy plate 940 are used in a manner which is similar to that of osteotomy implant 705 and osteotomy plate 740, but using two bone screws 950 to secure osteotomy plate 940 to the exterior of the bone and one bone screw 950 to secure osteotomy plate 940 to osteotomy implant 905 via bore 952 (FIG. 32). The provision of osteotomy plate 940 (with rim 955) and bone screws 950 help stabilize osteotomy implant 905 against retraction out of wedge-like opening W. In addition, osteotomy plate 940 can also help carry load between the two bone portions.

It should be appreciated that osteotomy plate 940 may also be used in conjunction with a ribbed implant, such as implant 205, etc.

Figure 34:
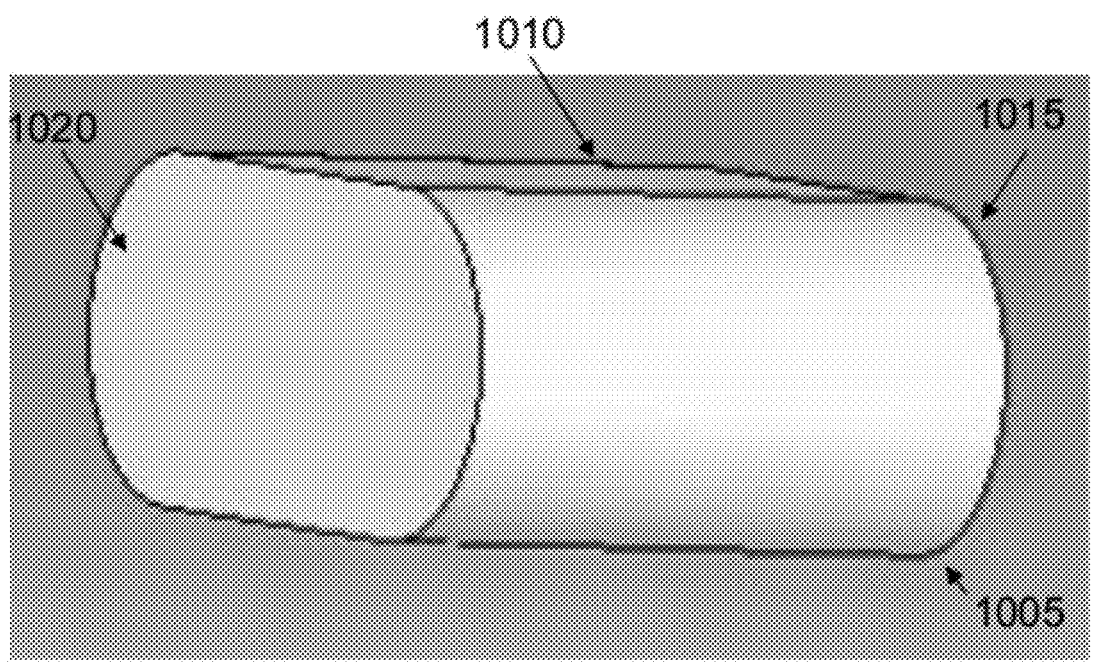
FIG. 34 is a schematic view showing a tenth novel osteotomy implant formed in accordance with the present invention.
Figure 35:
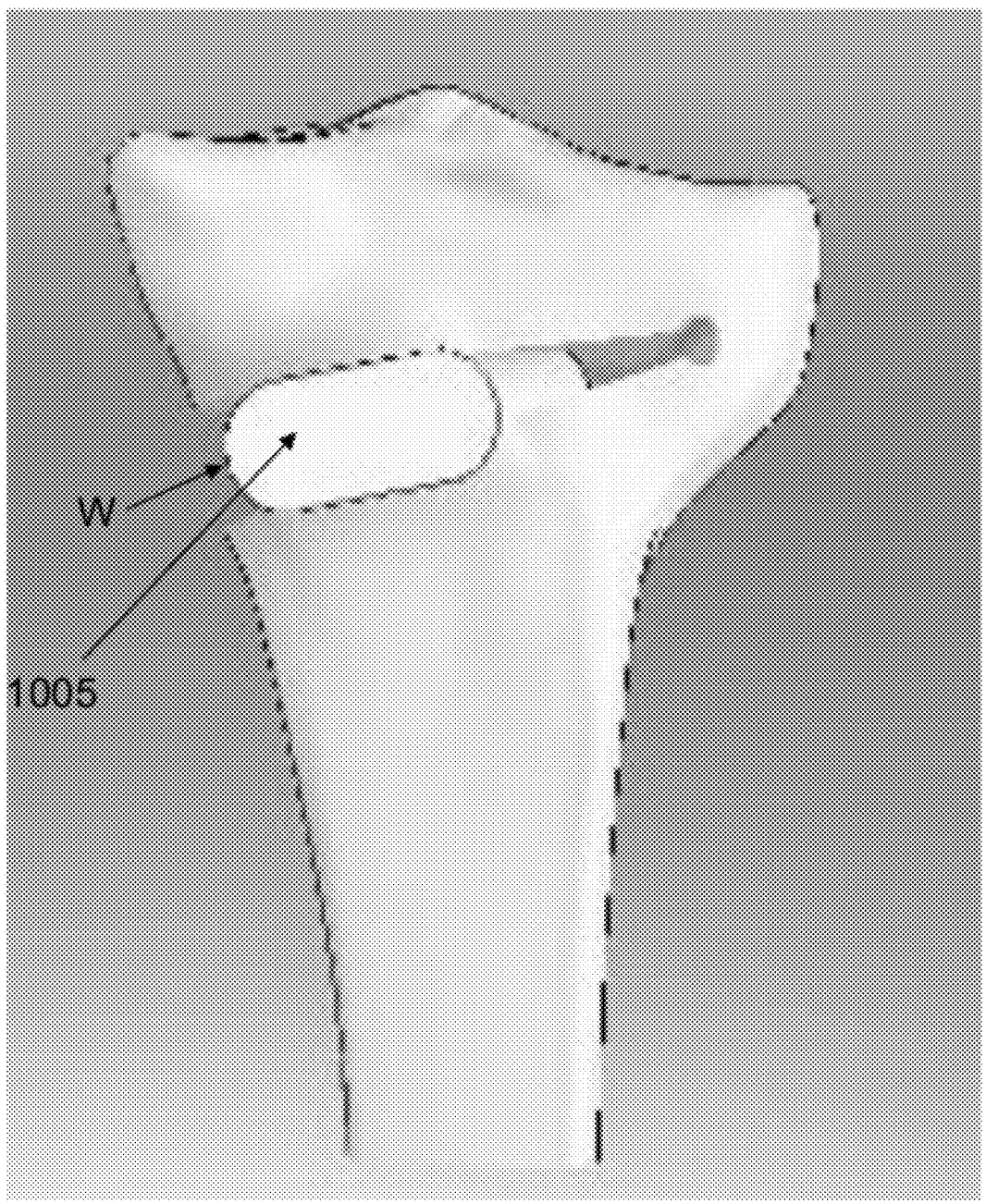
FIGS. 35 and 36 are schematic views showing the implant of FIG. 34 positioned within an osteotomy cut formed in the tibia.
Figure 36:
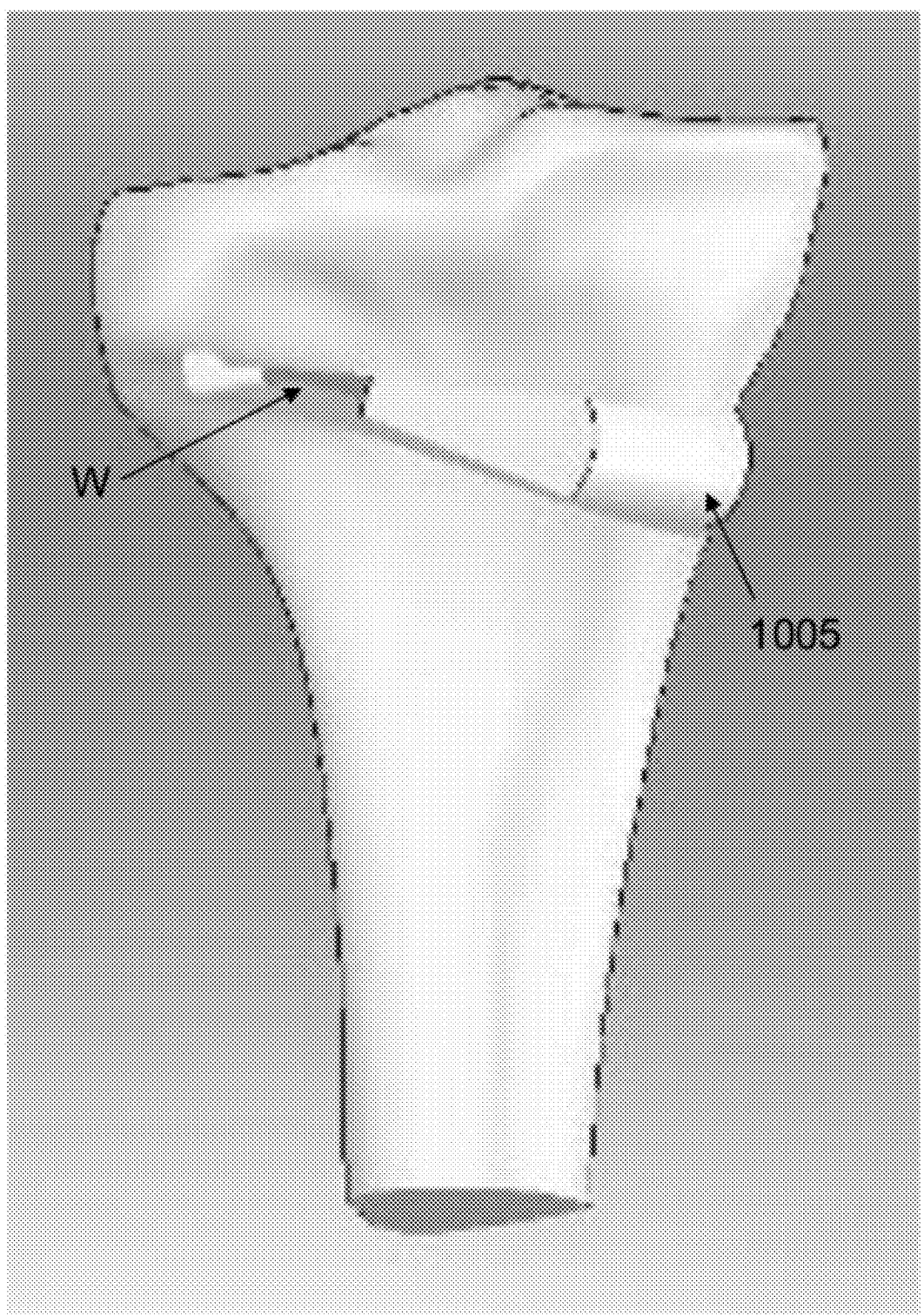

Looking next at FIGS. 34-36, there is shown a tenth novel osteotomy implant 1005 formed in accordance with the present invention. Osteotomy implant 1005 generally comprises an elongated body 1010 having a distal end 1015 and a proximal end 1020. Elongated body 1010 is formed with a smooth exterior, but may also be formed with a threaded or ribbed exterior (not shown). Similarly, elongated body 1010 may be formed with a tapered geometry or with a non-tapered geometry.

Osteotomy implant 1005 is positioned in wedge-like opening W in substantially the same manner as osteotomy implant 205, by using an appropriate inserter. Once osteotomy implant 1005 has been inserted to the appropriate depth within wedge-like opening W, osteotomy implant 1005 may be secured in position using toe pins, osteotomy plates, and/or bone screws, etc.

Figure 37:
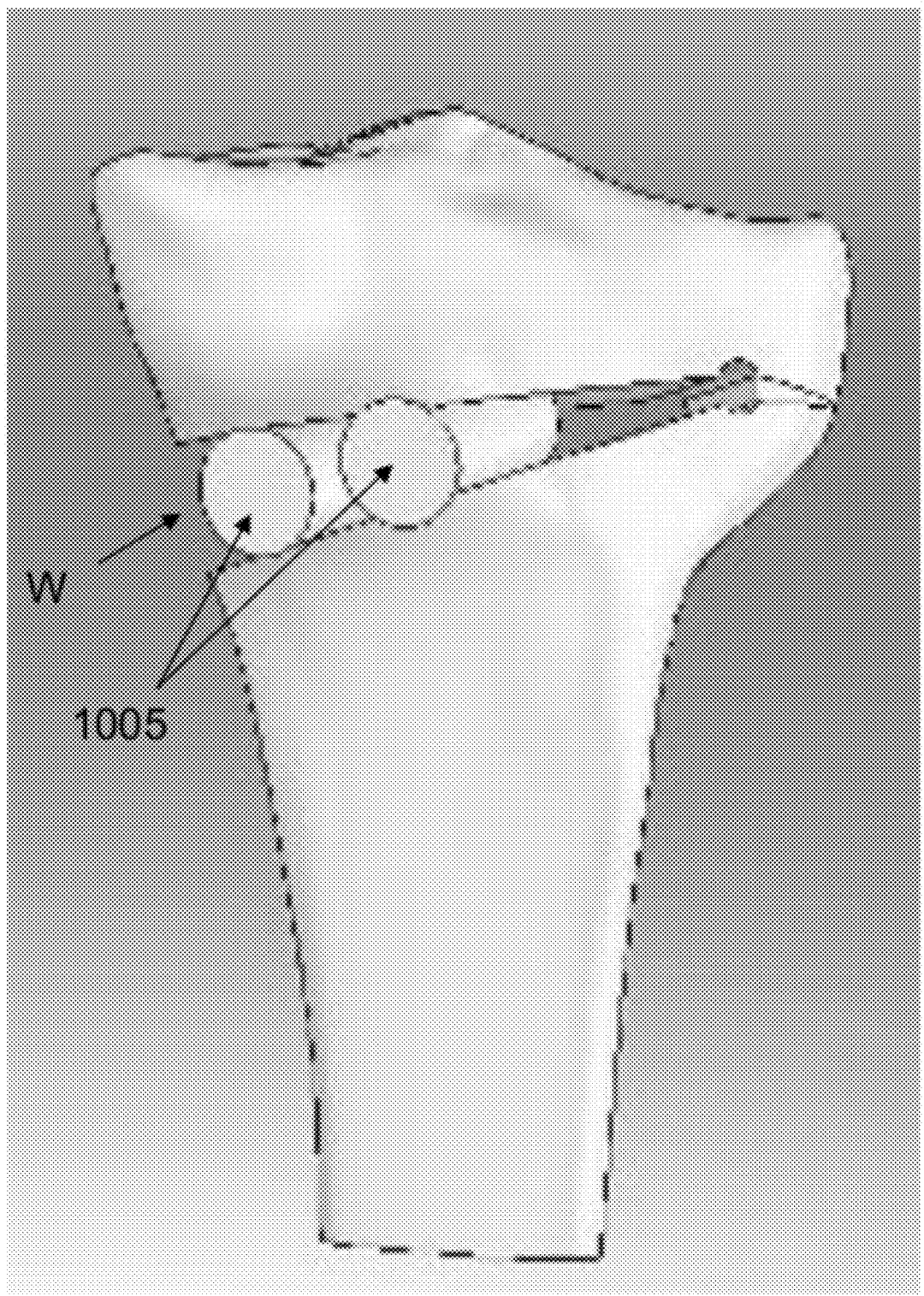
FIGS. 37-39 are schematic views showing a pair of novel osteotomy implants positioned within an osteotomy cut formed in the tibia.
Figure 38:
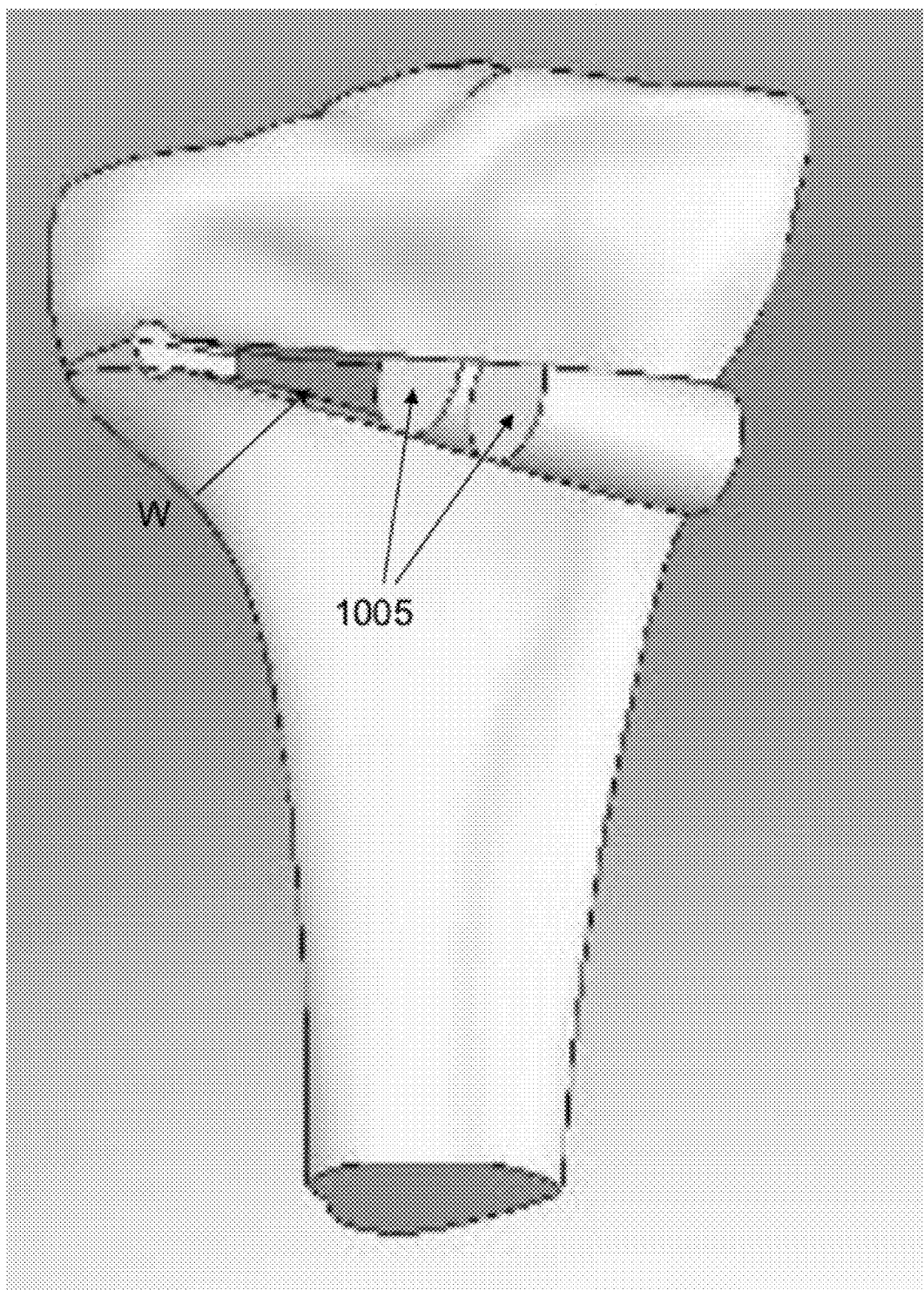
Figure 39:
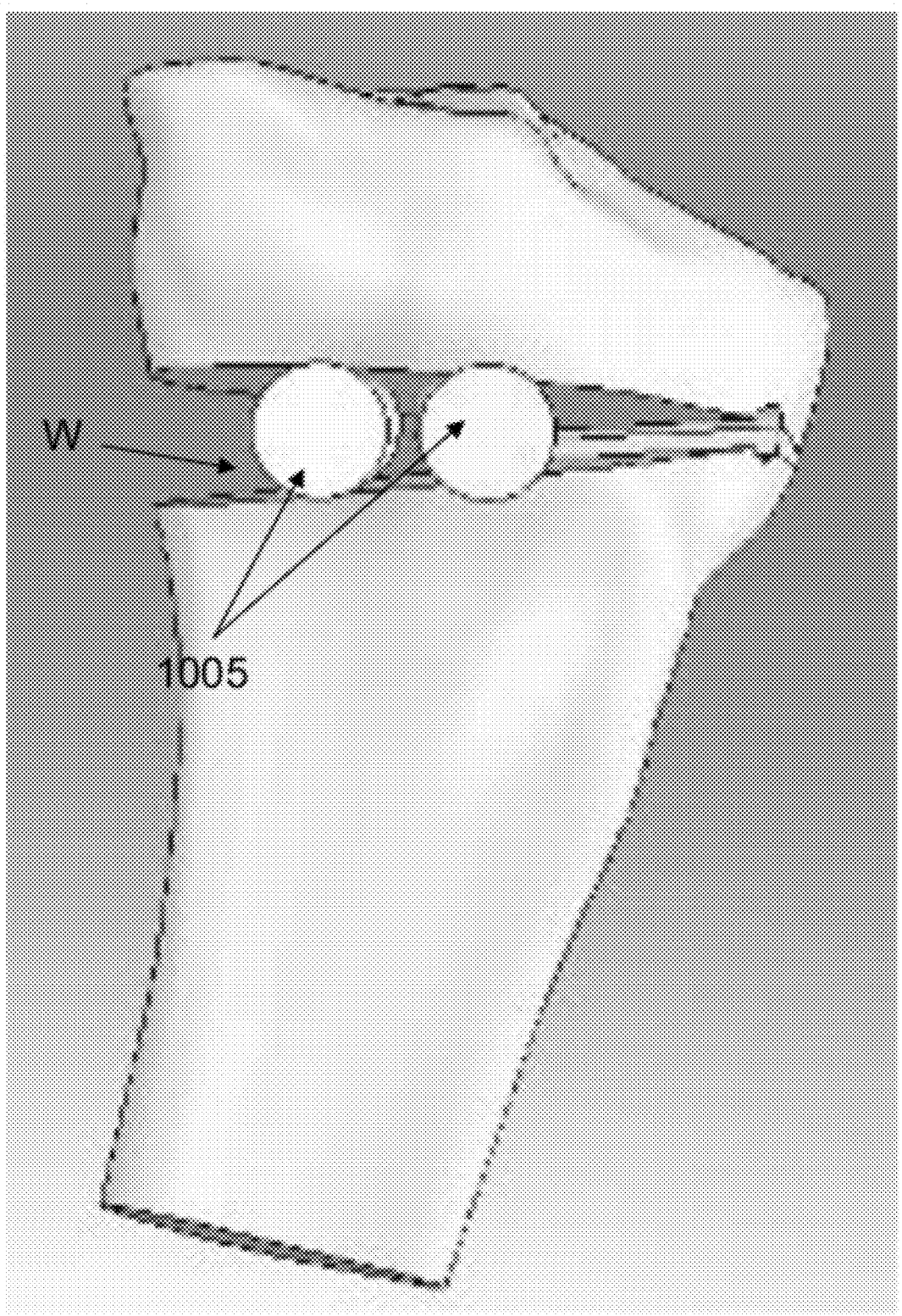

Looking next at FIGS. 37-39, two or more osteotomy implants 1005 may be disposed in wedge-like opening W in order to achieve the desired angle of correction. It should be appreciated that the two or more osteotomy implants 1005 may be disposed in wedge-like opening W in a side-by-side fashion (FIGS. 37-39) or in a serial fashion (not shown) depending on the approach and desired degree of correction.

It should also be appreciated that two or more osteotomy implants 1005 having different geometries, surfaces and/or tapered configurations may also be used in combination with one another.

Figure 40:
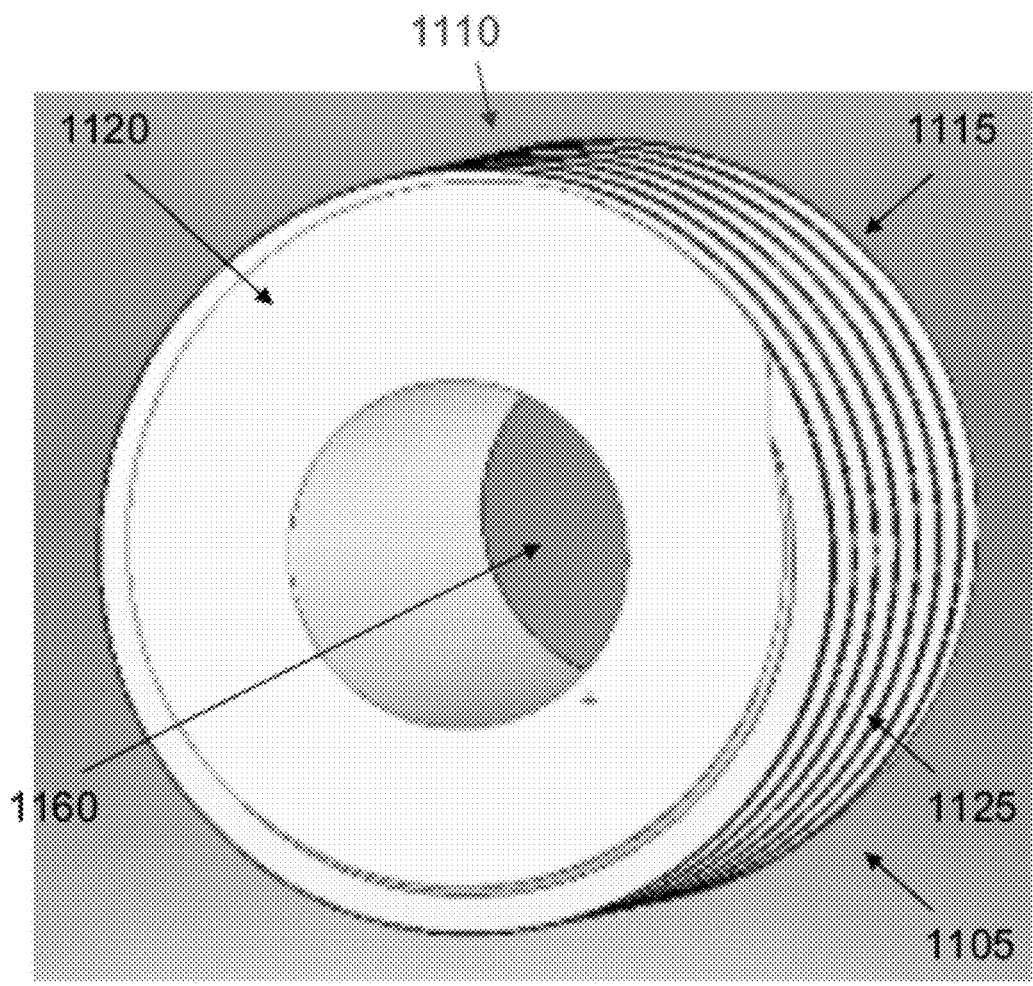
FIG. 40 is a schematic view showing an eleventh novel osteotomy implant formed in accordance with the present invention.

Looking next at FIG. 40, there is shown an eleventh novel osteotomy implant 1105 formed in accordance with the present invention. Osteotomy implant 1105 generally comprises an elongated body 1110 having a distal end 1115 and a proximal end 1120. Elongated body 1110 comprises a screw thread 1125 for engaging bone. Elongated body 1110 is provided with a center longitudinal fenestration 1160 to allow for increased bone growth into and through the implant during bone healing. It should be appreciated that osteotomy implant 1105 may be provided with a beveled distal end so as to facilitate insertion into bore B (or, in the case where no bore B is provided, directly into wedge-like opening W).

Osteotomy implant 1105 is positioned in wedge-like opening W in substantially the same manner as osteotomy implant 105, and by using an appropriate driver or inserter.

Figure 41:
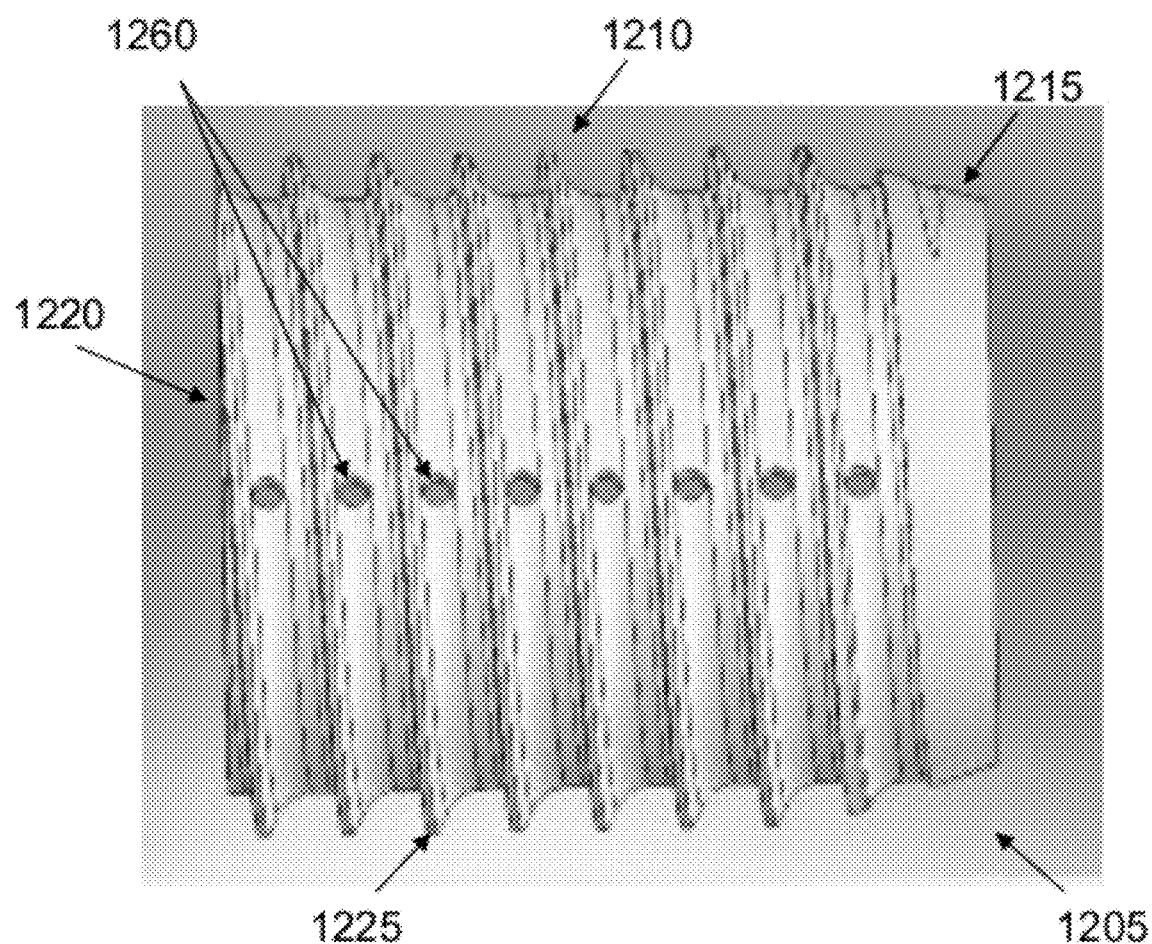
FIG. 41 is a schematic view showing a twelfth novel osteotomy implant formed in accordance with the present invention.

Looking next at FIG. 41, there is shown a twelfth novel osteotomy implant 1205 formed in accordance with the present invention. Osteotomy implant 1205 generally comprises an elongated body 1210 having a distal end 1215 and a proximal end 1220. Elongated body 1210 comprises a screw thread 1225 for engaging bone. Elongated body 1210 is provided with a beveled distal end so as to facilitate insertion into bore B (or, in the case where no bore B is provided, directly into wedge-like opening W). Elongated body 1210 is also provided with a plurality of sidewall fenestrations 1260 for increased bone growth into and through the implant during bone healing.

Osteotomy implant 1205 is positioned in wedge-like opening W in substantially the same manner as osteotomy implant 105, and by using an appropriate driver or inserter.

Figure 42:
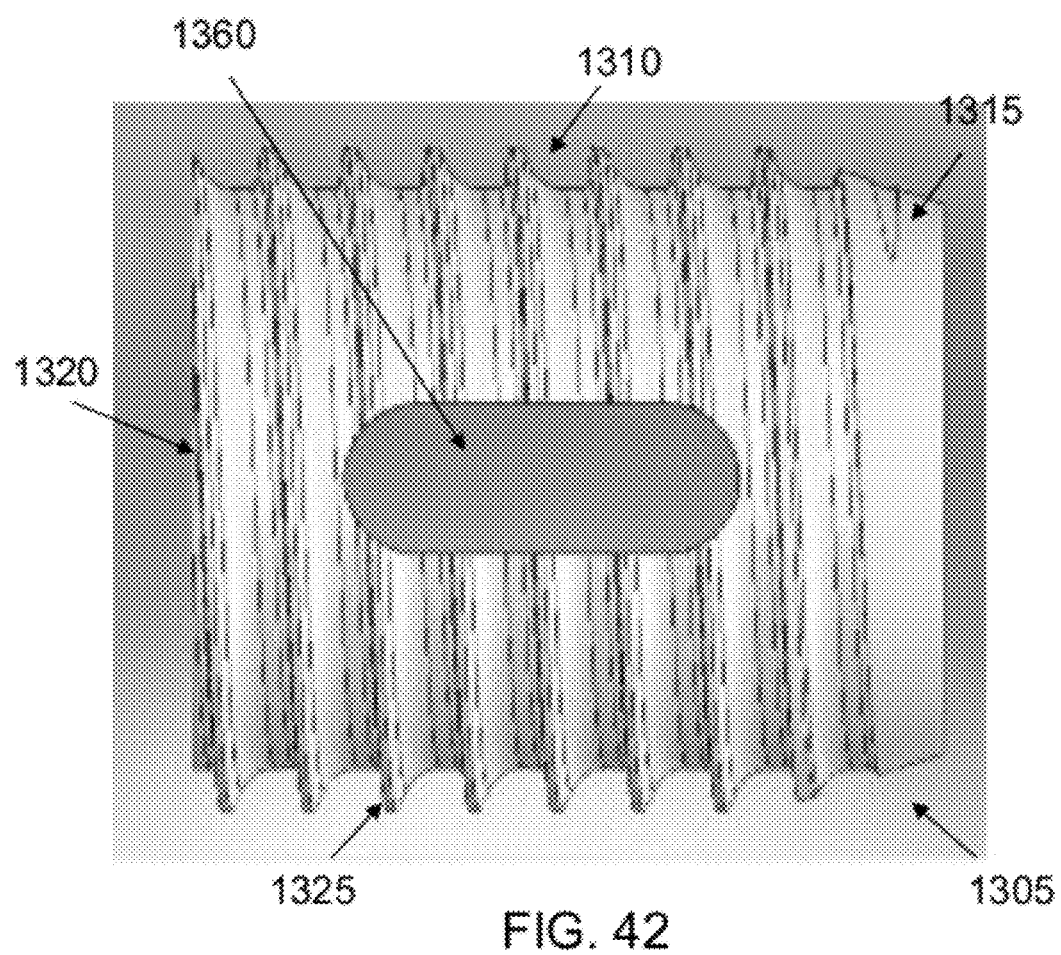
FIG. 42 is a schematic view showing a thirteenth novel osteotomy implant formed in accordance with the present invention.

Looking next at FIG. 42, there is shown a thirteenth novel osteotomy implant 1305 formed in accordance with the present invention. Osteotomy implant 1305 generally comprises an elongated body 1310 having a distal end 1315 and a proximal end 1320. Elongated body 1310 comprises a screw thread 1325 for engaging bone. Elongated body 1310 is provided with a beveled distal end so as to facilitate insertion into bore B (or, in the case where no bore B is provided, directly into wedge-like opening W). Elongated body 1310 is also provided with an elongated sidewall fenestration 1360 for increased bone growth into and through the implant during bone healing.

Osteotomy implant 1305 is positioned in wedge-like opening W in substantially the same manner as osteotomy implant 105, and by using an appropriate driver or inserter.

It should be appreciated that osteotomy implants 1105, 1205 and 1305 may all be used in combination with the toe pins, osteotomy plates and/or bone screws of the present invention, as well as with other toe pins, plates and bone screws well known in the art.

It should also be appreciated that the novel implants of the present invention may be formed out of plastic, metal, bone, bioabsorbable material, etc.

Significantly, it should be noted that the novel implants formed in accordance with the present invention provide surgeons with increased flexibility in performing an osteotomy procedure. Although the implants have been shown in use during a high tibial osteotomy, it will be appreciated that the implants could also be used in femoral osteotomy procedures, or in osteotomy procedures conducted on other bones.

Similarly, the novel implants may be used in a variety of approaches, angles, etc. Because the implants are formed with a generally symmetrical, non-anatomically-specific configuration, they can be deployed in a variety of ways. By way of example but not limitation, the implants may be used in an antero-medial approach, lateral approach, etc. Likewise, the implants of the present invention may be used in conjunction with an osteotomy cut formed using an apex pin in accordance with the methods of U.S. patent application Ser. No. 11/644,218, filed Dec. 22, 2006 by Kelly G. Ammann et al. for METHOD AND APPARATUS FOR PERFORMING AN OPENING WEDGE, HIGH TIBIAL OSTEOTOMY, which patent application is hereby incorporated herein by reference.

Lastly, the novel implants of the present invention are "one-size-fits-all", in the sense that a single implant can be advanced (or withdrawn) to an appropriate depth within the wedge-like opening so as to stabilize the bone portions with the desired degree of correction for each individual patient. This greatly reduces the need to inventory trial implants as well as different-shaped and different-sized osteotomy implants to account for variations in patient anatomy.

Anterio-Lateral Osteotomies

In the foregoing description, the present invention is discussed in the context of performing an open wedge osteotomy using an antero-medial approach so as to effect a medial opening wedge osteotomy. Of course, it should be appreciated that the present invention may also be used in antero-lateral approaches so as to effect a lateral opening wedge osteotomy, or in other approaches which will be well known to those skilled in the art.

Open wedge osteotomies can also be performed on the lower end of the femur (e.g., a so-called "open wedge, low femoral osteotomy") and/or on other bones.

The present invention may also be used in other types of osteomies, e.g., elbow, ankle, etc.

Modifications

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. A method for performing an open wedge osteotomy, the method comprising:
   forming a cut in a bone;
   manipulating the portions of the bone adjacent to the cut so as to open the cut into a wedge-like opening;
   providing an osteotomy implant, wherein the osteotomy implant comprises:
      an elongated body characterized by a distal end and proximal end, the elongated body having a screw thread thereon; positioning at least the distal end of the elongated body into the wedge-like opening so that the screw thread engages the surrounding bone; and
      an osteotomy plate for covering at least a portion of the entrance of the wedge-like opening; and
   threadingly advancing the elongated body into the wedge-like opening until the portions of the bone assume the desired positioning, with the elongated body stabilizing the bone portions in this position.

2. A method according to claim 1 wherein the osteotomy plate is secured to the bone after the elongated body is threadingly advanced into the wedge-like opening, whereby to prevent retraction of the elongated body out of the wedge-like opening.

3. A method according to claim 1 wherein the osteotomy plate is secured to the exterior of the bone using bone screws.

4. A method according to claim 1 wherein the osteotomy plate comprises a projection for engagement with the proximal end of the elongated body.

5. A method according to claim 4 wherein the projection encompasses the proximal end of the elongated body.

6. A method according to claim 4 wherein the elongated body comprises a recess, and further wherein the projection is sized to be received in the recess.

7. A method according to claim 1 wherein the elongated body comprises fenestrations formed therethrough.

8. A method for performing an open wedge osteotomy, the method comprising:
   forming a cut in a bone;
   manipulating the portions of the bone adjacent to the cut so as to open the cut into a wedge-like opening;
   providing an osteotomy implant, wherein the osteotomy implant comprises:
      an elongated body characterized by a distal end and proximal end, the elongated body having a screw thread thereon and a crossbore for receiving a fixation element therethrough;
   positioning at least the distal end of the elongated body into the wedge-like opening so that the screw thread engages the surrounding bone;
   threadingly advancing the elongated body into the wedge-like opening until the portions of the bone assume the desired positioning, with the elongated body stabilizing the bone portions in this position; and
   passing a fixation element through the crossbore and into the bone after the elongated body has been threadingly advanced into the wedge-like opening.

9. A method according to claim 8 wherein the elongated body is tapered distally so as to facilitate positioning and advancement of the elongated body into the wedge-like opening.

10. A method according to claim 9 wherein the elongated body is tapered along its entire length.

11. A method according to claim 8 wherein the proximal end of the elongated body is provided with a recess for receiving an appropriate driver used to threadingly advance the elongated body into the wedge-like opening.

12. A method according to claim 8 wherein the fixation element comprises a toe screw.

13. A method according to claim 8 wherein the fixation element comprises a toe pin.

14. A method according to claim 8 further comprising the step of drilling a bore in the bone, with the distal end of the elongated body being positioned in the bore prior to threadingly advancing the elongated body into the wedge-like opening.

15. A method according to claim 14 wherein the bore is drilled after the wedge-like opening has been created.

16. A method according to claim 15 wherein the bore is over-drilled relative to the wedge-like opening.

17. A method for performing an open wedge osteotomy, the method comprising:
   forming a cut in a bone;
   manipulating the portions of the bone adjacent to the cut so as to open the cut into a wedge-like opening;
   providing an osteotomy implant, wherein the osteotomy implant comprises an elongated body characterized by a distal end and proximal end, the elongated body having a screw thread thereon; positioning at least the distal end of the elongated body into the wedge-like opening so that the screw thread engages the surrounding bone;
   threadingly advancing the elongated body into the wedge-like opening until the portions of the bone assume the desired positioning, with the elongated body stabilizing the bone portions in this position; and
   drilling a bore in the bone, with the distal end of the elongated body being positioned in the bore prior to threadingly advancing the elongated body into the wedge-like opening, wherein the bore is drilled before the wedge-like opening has been created.

18. A method according to claim 17 wherein the bore is drilled after the cut has been formed in the bone.

19. A method for performing an open wedge osteotomy, the method comprising:
   forming a cut in a bone;
   manipulating the portions of the bone adjacent to the cut so as to open the cut into a wedge-like opening;
   providing an osteotomy implant, wherein the osteotomy implant comprises:
      an elongated body characterized by a distal end and proximal end, the elongated body having a screw thread thereon and a crossbore for receiving a fixation element therethrough, wherein one end of the crossbore opens on the proximal end of the elongated body and the other end of the crossbore opens intermediate the elongated body;
   positioning at least the distal end of the elongated body into the wedge-like opening so that the screw thread engages the surrounding bone; and
   threadingly advancing the elongated body into the wedge-like opening until the portions of the bone assume the desired positioning, with the elongated body stabilizing the bone portions in this position.

* * * * *